United States Patent
Colton et al.

(10) Patent No.: US 9,816,070 B2
(45) Date of Patent: Nov. 14, 2017

(54) ARTICLES AND METHODS FOR STEM CELL DIFFERENTIATION

(71) Applicant: Massachusetts Institute of Technology, Cambridge, MA (US)

(72) Inventors: Clark K. Colton, Newton, MA (US); Karen K. Gleason, Cambridge, MA (US); Anna M. Coclite, Bari (IT); Amanda R. Dilenno, Boston, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/304,841

(22) Filed: Jun. 13, 2014

(65) Prior Publication Data
US 2014/0370598 A1    Dec. 18, 2014

Related U.S. Application Data

(60) Provisional application No. 61/835,326, filed on Jun. 14, 2013.

(51) Int. Cl.
  *C12N 5/00*  (2006.01)
  *C12N 5/0735*  (2010.01)
  *C12N 5/071*  (2010.01)

(52) U.S. Cl.
  CPC ......... *C12N 5/0068* (2013.01); *C12N 5/0606* (2013.01); *C12N 5/0676* (2013.01);
  (Continued)

(58) Field of Classification Search
  None
  See application file for complete search history.

(56) References Cited

U.S. PATENT DOCUMENTS 5,134,057 A * 7/1992 Kuypers ............... G03F 7/016
                                                        424/423
5,314,960 A * 5/1994 Spinelli ............... C08F 287/00
                                                        525/280
(Continued)

FOREIGN PATENT DOCUMENTS

WO    WO 00/29550 A2    5/2000
WO    WO 2008/156708    12/2008
(Continued)

OTHER PUBLICATIONS

Ai, Hua; et al; "Biocompatibility of layer-by-layer self-assembled nanofilm on silicone rubber for neurons" Journal of Neuroscience Methods, 128, 1-8, 2003.*
(Continued)

*Primary Examiner* — David Berke-Schlessel
(74) *Attorney, Agent, or Firm* — Wolf, Greenfield & Sacks, P.C.

(57) ABSTRACT

Articles and methods for stem cell differentiation are generally described. In some embodiments, an article for stem cell differentiation may comprise an oxygen permeable substrate having at least a portion of a surface coated with a matrix. The matrix may allow the surface chemistry of the substrate to be altered, such that the cell-substrate surface interactions may be finely controlled without substantially affecting the oxygen permeability of the substrate. The surface chemistry may be altered to promote directed stem cell differentiation by, e.g., modification of the matrix surface with a specific density of biological molecules. In some embodiments, methods for stem cell differentiation may comprise directing the differentiation of stem cells on the articles, described herein, under suitable environmental conditions. Articles and methods, described herein, may be free of xenogeneic components and particularly well-suited for
(Continued)

applications involving the differentiation of human stem cells into specific lineages.

13 Claims, 7 Drawing Sheets

(52) U.S. Cl.
CPC ...... *C12N 2506/02* (2013.01); *C12N 2533/30* (2013.01); *C12N 2533/50* (2013.01); *C12N 2539/00* (2013.01)

(56) References Cited

U.S. PATENT DOCUMENTS

| | | | |
|---|---|---|---|
| 5,942,435 | A | 8/1999 | Wheeler |
| 6,534,052 | B1 | 3/2003 | Xiao et al. |
| 6,613,568 | B2 | 9/2003 | Kaufman et al. |
| 6,833,269 | B2 | 12/2004 | Carpenter |
| 7,033,831 | B2 | 4/2006 | Fisk et al. |
| 7,250,294 | B2 | 7/2007 | Carpenter et al. |
| 7,282,366 | B2 | 10/2007 | Rambhatla et al. |
| 7,326,572 | B2 | 2/2008 | Fisk et al. |
| 7,425,448 | B2 | 9/2008 | Xu |
| 7,732,199 | B2 | 6/2010 | Xu et al. |
| 7,763,464 | B2 | 7/2010 | Xu |
| 9,029,147 | B2 | 5/2015 | Colton et al. |
| 2002/0120084 | A1* | 8/2002 | Valint, Jr. ............ A61L 27/34 526/260 |
| 2005/0164382 | A1 | 7/2005 | Xu |
| 2005/0266554 | A1 | 12/2005 | D'Amour et al. |
| 2007/0259421 | A1 | 11/2007 | D'Amour et al. |
| 2010/0261277 | A1 | 10/2010 | Colton et al. |
| 2011/0312087 | A1 | 12/2011 | Khan |
| 2012/0219532 | A1 | 8/2012 | Colton et al. |
| 2013/0287743 | A1 | 10/2013 | Colton et al. |

FOREIGN PATENT DOCUMENTS

| | | |
|---|---|---|
| WO | WO 2009/007852 A2 | 1/2009 |
| WO | WO 2009/035217 A1 | 3/2009 |
| WO | WO 2009/079007 A1 | 6/2009 |
| WO | WO 2011/005326 | 1/2011 |

OTHER PUBLICATIONS

Kobayashi, Hisatoshi; Ikada, Yoshito; "Corneal cell adhesion and proliferation on hydrogel sheets bound with cell-adhesive proteins" Current Eye Research, 10, 899-908, 1991.*

Bonakdar, Shahin; et al; "Preparation and characterization of polyvinyl alcohol hydrogels crosslinked by biodegradable polyurethane for tissue engineering of cartilage" Materials Science and Engineering C, 30, 636-643, 2010.*

Monge, Sophie; et al; "Improvement of Silicone Endothelialization by Treatmentwith Allylamine and/or Acrylic Acid Low-Pressure Plasma" Journal of Applied Polymer Science, 87, 1794-1802, 2003.*

International Search Report and Written Opinion dated Sep. 26, 2014 for Application No. PCT/US2014/042424.

Bose et al., Initiated CVD of poly(2-hydroxyethyl methacrylate) hydrogels: synthesis, characterization and in-vitro biocompatibility. Chem Vap Deposition. Jun. 1, 2009; 15(4/5/6):150-5. doi: 10.1002/cvde.200806748.

Coclite et al., Controlling the degree of crystallinity and preferred crystallographic orientation in poly-perfluorodecylacrylate thin films by initiated chemical vapor deposition. Adv Funct Mater. May 23, 2012; 22(10):2167-76. Epub Feb. 23, 2012. doi: 10.1002/adfm.201103035.

Ozaydin-Ince et al., CVD of polymeric thin films: applications in sensors, biotechnology, microelectronics/organic electronics, microfluidics, MEMS, composites and membranes. Rep Prog Phys. Dec. 16, 2011;75(1):016501. doi:10.1088/0034-4885/75/1/016501. 40 pages.

Powers et al., Accurate control of oxygen level in cells during culture on silicone rubber membranes with application to stem cell differentiation. Biotechnol Prog. May-Jun. 2010;26(3):805-18. doi: 10.1002/btpr.359.

[No Author Listed], FDA Center for Biologics Evaluation and Research: Cellular, Tissue, and Gene Therapeutics Advisory Committee, Summary Minutes. Meeting #45. Apr. 10-11, 2008. 7 pages.

[No Author Listed], Innovative cell culture devices to help expand your growth. Wilson Wolf Manufacturing, Inc. http://www.wilsonwolf.com/technology.htm [last accessed Jun. 4, 2008]. 1 page.

Abaci et al., Adaptation to oxygen deprivation in cultures of human pluripotent stem cells, endothelial progenitor cells, and umbilical vein endothelial cells. Am J Physiol Cell Physiol. Jun. 2010;298(6):C1527-37. doi: 10.1152/ajpcell.00484.2009. Epub Feb. 24, 2010.

Ai et al., Biocompatibility of layer-by-layer self-assembled nanofilm on silicone rubber for neurons. J Neurosci Methods. Sep. 30, 2003;128(1-2):1-8.

Avgoustiniatos, Oxygen diffusion limitations in pancreatic islet culture and immunoisolation. Thesis; Massachusetts Institute of Technology. Feb. 2002 648 pages.

Baharvand et al., Differentiation of human embryonic stem cells into hepatocytes in 2D and 3D culture systems in vitro. Int J Dev Biol. 2006;50(7):645-52.

Bauwens et al., Development of a perfusion fed bioreactor for embryonic stem cell-derived cardiomyocyte generation: oxygen-mediated enhancement of cardiomyocyte output. Biotechnol Bioeng. May 20, 2005;90(4):452-61.

Bjorklund et al., Embryonic stem cells develop into functional dopaminergic neurons after transplantation in a Parkinson rat model. Proc Natl Acad Sci U S A. Feb. 19, 2002;99(4):2344-9.Epub Jan. 8, 2002.

Blum et al., Clonal analysis of human embryonic stem cell differentiation into teratomas. Stem Cells. Aug. 2007;25(8):1924-30. Epub Apr. 26, 2007.

Blum et al., The tumorigenicity of human embryonic stem cells. Adv Cancer Res. 2008;100:133-58.

Bondue et al., Mesp1 acts as a master regulator of multipotent cardiovascular progenitor specification. Cell Stem Cell. Jul. 3, 2008;3(1):69-84.

Bonner-Weir et al., In vitro cultivation of human islets from expanded ductal tissue. Proc Natl Acad Sci U S A. Jul. 5, 2000;97(14):7999-8004.

Brederlau et al., Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.

Brunelle et al., Oxygen deprivation induced cell death: an update. Apoptosis. Dec. 2002;7(6):475-82.

Brusselmans et al., A novel role for vascular endothelial growth factor as an autocrine survival factor for embryonic stem cells during hypoxia. J Biol Chem. Feb. 4, 2005;280(5):3493-9. Epub Nov. 29, 2004.

Caspi et al., Transplantation of human embryonic stem cell-derived cardiomyocytes improves myocardial performance in infarcted rat hearts. J Am Coll Cardiol. Nov. 6, 2007;50(19):1884-93. Epub Oct. 23, 2007.

Coclite et al., Initiated PECVD of Organosilicon Coatings: A New Strategy to Enhance Monomer Structure Retention. Plasma Process. Polym. Feb. 17, 2012;9(4):425-34. doi: 10.1002/ppap.201100167.

Csete, Oxygen in the cultivation of stem cells. Ann N Y Acad Sci. May 2005;1049:1-8.

Cunningham et al., Quantification of fibronectin adsorption to silicone-rubber cell culture substrates. Biotechniques. Apr. 2002;32(4):876-87.

D'Amour et al., Efficient differentiation of human embryonic stem cells to definitive endoderm. Nat Biotechnol. Dec. 2005;23(12):1534-41. Epub Oct. 28, 2005.

(56) References Cited

OTHER PUBLICATIONS

D'Amour et al., Production of pancreatic hormone-expressing endocrine cells from human embryonic stem cells. Nat Biotechnol. 2006 Nov. 2006;24(11):1392-401. Epub Oct. 19, 2006.
Daley et al., Realistic prospects for stem cell therapeutics. Hematol. Am Soc Hematol Educ Program. 2003:398-418.
Damjanov et al., The terminology of teratocarcinomas and teratomas. Nat Biotechnol. Nov. 2007;25(11):1212.
Dang et al., Controlled, scalable embryonic stem cell differentiation culture. Stem Cells. 2004;22(3):275-82.
David et al., MesP1 drives vertebrate cardiovascular differentiation through Dkk-1-mediated blockade of Wnt-signalling. Nat Cell Biol. Mar. 2008;10(3):338-45. Epub Feb. 24, 2008.
Diienno et al., Controlled Oxygen Markedly Influences Differentiation of Embryonic Stem Cells to Insulin Producing Cells. ISSCR 10th Annual Meeting, Yokohama, Japan. Abstract. Jun. 13-16, 2012 1 page.
Diienno et al., Stable Feeder-and Xeno-free Surgaces for Long-term Growth of Undifferentiated Human Embryonic Stem Cells. Poster. Cambridge, Massachusetts. MIT: Department of Engineering. Jul. 8, 2013 1 page.
Diienno et al., Variation of Oxygen in a Controlled Manner Markedly Enhances Multi-Stage Differentiation of Embryonic Stem Cells to Insulin Producing Cells. Biomedical Applications of Chemical Engineering 2012 Annual Meeting. Abstract. Oct. 31, 2012 4 pages.
Drukker et al., Human embryonic stem cells and their differentiated derivatives are less susceptible to immune rejection than adult cells. Stem Cells. Feb. 2006;24(2):221-9. Epub Aug. 18, 2005.
Erdö et al., Host-dependent tumorigenesis of embryonic stem cell transplantation in experimental stroke. J Cereb Blood Flow Metab. Jul. 2003;23(7):780-5.
Feeling et al., Tracking mesoderm induction and its specification to the hemangioblast during embryonic stem cell differentiation. Development. Sep. 2003;130(17):4217-27.
Fernandes et al., Different stages of pluripotency determine distinct patterns of proliferation, metabolism, and lineage commitment of embryonic stem cells under hypoxia. Stem Cell Res. Jul. 2010;5(1):76-89. Epub Apr. 22, 2010.
Fraker et al., Enhanced oxygenation promotes beta-cell differentiation in vitro. Stem Cells. Dec. 2007;25(12):3155-64. Epub Aug. 30, 2007.
Fukuda et al., Stem cells as a source of regenerative cardiomyocytes. Circ Res. Apr. 28, 2006;98(8):1002-13.
Gerecht-Nir et al., Human embryonic stem cells as an in vitro model for human vascular development and the induction of vascular differentiation. Lab Invest. Dec. 2003;83(12):1811-20.
Ginis et al., Differences between human and mouse embryonic stem cells. Dev Biol. May 15,2004 15;269(2):360-80.
Grapin-Botton et al., Endoderm development: from patterning to organogenesis. Trends Genet. Mar. 2000;16(3):124-30.
Gu et al., Direct lineage tracing reveals the ontogeny of pancreatic cell fates during mouse embryogenesis. Mech Dev. Jan. 2003;120(1):35-43.
Hamon et al., Direct oxygen supply with polydimethylsiloxane (PDMS) membranes induces a spontaneous organization of thick heterogeneous liver tissues from rat fetal liver cells in vitro. Cell Transplant. 2012;21(2-3):401-10. doi: 10.3727/096368911X605303.
Hentze et al., Cell therapy and the safety of embryonic stem cell-derived grafts. Trends Biotechnol. Jan. 2007;25(1):24-32. Epub Nov. 3, 2006.
Hoffman et al., Characterization and culture of human embryonic stem cells. Nat Biotechnol. Jun. 2005;23(6):699-708.
Horton et al., Engineering microenvironments for embryonic stem cell differentiation to cardiomyocytes. Regen Med. Sep. 2009;4(5):721-32.
Hrvatin et al., Differentiated human stem cells resemble fetal, not adult, β cells. Proc Natl Acad Sci. Feb. 25, 2014;111(8):3038-43. doi: 10.1073/pnas.1400709111.
Humphrey et al., Maintenance of pluripotency in human embryonic stem cells is STAT3 independent. Stem Cells. 2004;22(4):522-30.
Jaenisch et al., Stem cells, the molecular circuitry of pluripotency and nuclear reprogramming. Cell. Feb. 22, 2008;132(4):567-82.
Jensen et al., Diffusion in tissue cultures on gas-permeable and impermeable supports. J Theor Biol. Feb. 1976;56(2):443-58.
Kaufman et al., Hematopoietic colony-forming cells derived from human embryonic stem cells. Proc Natl Acad Sci U S A. Sep. 11, 2001;98(19):10716-21. Epub Sep. 4, 2001.
Kehat et al., Human embryonic stem cells for myocardial regeneration. Heart Fail Rev. Jul. 2003;8(3):229-36.
Keller. Embryonic stem cell differentiation: emergence of a new era in biology and medicine. Genes Dev. May 15, 2005;19(10):1129-55.
Kim et al., Dopamine neurons derived from embryonic stem cells function in an animal model of Parkinson's disease. Nature. Jul. 4, 2002;418(6893):50-6. Epub Jun. 20, 2002.
Kim et al., Increase in dopaminergic neurons from mouse embryonic stem cell-derived neural progenitor/stem cells is mediated by hypoxia inducible factor-1alpha. J Neurosci Res. Aug. 15, 2008;86(11):2353-62.
Klug et al., Genetically selected cardiomyocytes from differentiating embronic stem cells form stable intracardiac grafts. J Clin Invest. Jul. 1, 1996;98(1):216-24.
Koay et al., Hypoxic chondrogenic differentiation of human embryonic stem cells enhances cartilage protein synthesis and biomechanical functionality. Osteoarthritis Cartilage. Dec. 2008;16(12):1450-6. Epub Jun. 9, 2008.
Kroon et al., Pancreatic endoderm derived from human embryonic stem cells generates glucose-responsive insulin-secreting cells in vivo. Nat Biotechnol. Apr. 2008;26(4):443-52. Epub Feb. 20, 2008.
Kurosawa et al., Effect of oxygen on in vitro differentiation of mouse embryonic stem cells. J Biosci Bioeng. Jan. 2006;101(1):26-30.
Laflamme et al., Cardiomyocytes derived from human embryonic stem cells in pro-survival factors enhance function of infarcted rat hearts. Nat Biotechnol. Sep. 2007;25(9):1015-24. Epub Aug. 26, 2007.
Lam et al., Multipotent progenitor cells in regenerative cardiovascular medicine. Pediatr Cardiol. Jul. 2009;30(5):690-8. Epub May 5, 2009.
Lavon et al., Differentiation and isolation of hepatic-like cells from human embryonic stem cells. Differentiation. Jun. 2004;72(5):230-8.
Lawrenz et al., Highly sensitive biosafety model for stem-cell-derived grafts. Cytother. 2004;6(3):212-22.
Lee et al., Efficient generation of midbrain and hindbrain neurons from mouse embryonic stem cells. Nat Biotechnol. Jun. 2000;18(6):675-9.
Lensch et al., The terminology of teratocarcinomas and teratomas. Nat Biotechnol. Nov. 2007;25(11):1211; author reply 1211-2.
Leor et al., Human embryonic stem cell transplantation to repair the infarcted myocardium. Heart. Oct. 2007;93(10):1278-84. Epub Jun. 12, 2007.
Lindsley et al., Mesp1 coordinately regulates cardiovascular fate restriction and epithelial-mesenchymal transition in differentiating ESCs. Cell Stem Cell. Jul. 3, 2008;3(1):55-68.
Ma et al., Hypoxia and stem cell-based engineering of mesenchymal tissues. Biotechnol Prog. Jan.-Feb. 2009;25(1):32-42. doi: 10.1002/btpr.128. Epub Jan. 1, 2010 18 pages.
Mclimans et al., Kinetics of gas diffusion in mammalian cell culture systems. I. Experimental. Biotechnol Bioeng. Nov. 1968;10:725-40.
Mei et al., Combinatorial development of biomaterials for clonal growth of human pluripotent stem cells. Nat Mater. Sep. 2010;9(9):768-78. doi: 10.1038/nmat2812. Epub Jul. 3, 2012 22 pages.
Melkoumian et al, Synthetic peptide-acrylate surfaces for long-term self-renewal and cardiomyocyte differentiation of human embryonic stem cells. Nat Biotech. Jun. 2010;28(6):606-10. Epub May 30, 2010. doi:10.1038/nbt.1629.
Mfopou et al., Efficient definitive endoderm induction from mouse embryonic stem cell adherent cultures: A rapid screening model for differentiation studies. Stem Cell Res. 2014;12:166-77.

(56) References Cited

OTHER PUBLICATIONS

Millman et al., Culture under low oxygen conditions markedly enhances differentiation of murine embryonic stem cells into cardiomyocytes, The 5$^{th}$ International Society for Stem Cell Research (ISSCR) Annual Meeting, Cairns, Australia. Jun. 17-20, 2007 1 page.

Millman et al., Differentiation of murine embryonic stem cells under low oxygen influences cardiomyocyte yield and timing and magnitude of cardiomyocyte gene expression. NIH Symposium on Cardiovascular Regenerative Medicine, Bethesda, MD. Oct. 14-15, 2009 1 page.

Millman et al., Extended Low Oxygen Culture of Mouse Embryonic Stem Cells Reduces the Fraction of Tumor-Forming Residual Pluripotent Cells in Differentiated Populations. NIH Symposium on Cardiovascular Regenerative Medicine, Bethesda, MD. Oct. 14-15, 1 page.

Millman et al., Low oxygen influences the self-renewal and differentiation of murine embryonic stem cells, The 6$^{th}$ International Society for Stem Cell Research (ISSCR) Annual Meeting, Philadelphia, PA. Jun 11-14, 2008 1 page.

Millman et al., The effects of low oxygen on self-renewal and differentiation of embryonic stem cells. Curr Opin Organ Transplant. Dec. 2009;14(6):694-700.

Mondragon-Teran et al., Lowering oxygen tension enhances the differentiation of mouse embryonic stem cells into neuronal cells. Biotechnol Prog. Sep.-Oct. 2009;25(5):1480-8.

Niebruegge et al., Generation of human embryonic stem cell-derived mesoderm and cardiac cells using size-specified aggregates in an oxygen-controlled bioreactor. Biotechnol Bioeng. Feb. 1, 2009;102(2):493-507.

Nir et al., Human embryonic stem cells for cardiovascular repair. Cardiovasc Res. May 1, 2003;58(2):313-23.

Okazaki et al., Oxygen, epigenetics and stem cell fate. Regen Med. Jan. 2006;1(1):71-83.

Papas et al., High-density culture of human islets on top of silicone rubber membranes. Transplant Proc. Oct. 2005;37(8):3412-4.

Pei, Regulation of pluripotency and reprogramming by transcription factors. J Biol Chem. Feb. 6, 2009;284(6):3365-9. Epub Sep. 26, 2008.

Pera et al., Regulation of human embryonic stem cell differentiation by BMP-2 and its antagonist noggin. J Cell Sci. Mar. 1, 2004;117(Pt 7):1269-80.

Petruczok et al., Controllable Cross-Linking of Vapor-Deposited Polymer Thin Films and Impact on Material Properties. Macromolecules. Amer Chem Soc. Feb. 28, 2013;46(5):1832-40. doi: dx.doi.org/10.1021/ma302566r.

Powers et al., Effects of oxygen on mouse embryonic stem cell growth, phenotype retention, and cellular energetics. Biotechnol Bioeng. Oct. 1, 2008;101(2):241-54.

Przyborski, Differentiation of human embryonic stem cells after transplantation in immune-deficient mice. Stem Cells. Oct. 2005;23(9):1242-50.

Purpura et al., Soluble Flt-1 regulates Flk-1 activation to control hematopoietic and endothelial development in an oxygen-responsive manner. Stem Cells. Nov. 2008;26(11):2832-42. Epub Sep. 4, 2008.

Rambhatla et al., Generation of hepatocyte-like cells from human embryonic stem cells. Cell Transplant. 2003;12(1):1-11.

Ramirez et al., Effect of Oxygen tension and substrate on growth and differentiation of mouse embryonic stem cells. Reprod Fertil Dev. 2006;18(2):209-10.

Ramírez-Bergeron et al., Hypoxia affects mesoderm and enhances hemangioblast specification during early development. Development. Sep. 2004;131(18):4623-34.

Ramírez-Bergeron et al., Hypoxia-inducible factor and the development of stem cells of the cardiovascular system. Stem Cells. 2001;19(4):279-86.

Sato et al., Maintenance of pluripotency in human and mouse embryonic stem cells through activation of Wnt signaling by a pharmacological GSK-3-specific inhibitor. Nat Med. Jan. 2004;10(1):55-63. Epub Dec. 21, 2003.

Schwartz et al., Defined conditions for development of functional hepatic cells from human embryonic stem cells. Stem Cells Dev. Dec. 2005;14(6):643-55.

Semenza et al., Regulation of cardiovascular development and physiology by hypoxia-inducible factor 1. Ann N Y Acad Sci. Jun. 1999 30;874:262-8.

Shih et al., Human embryonic stem cells are prone to generate primitive, undifferentiated tumors in engrafted human fetal tissues in severe combined immunodeficient mice. Stem Cells Dev. Dec. 2007;16(6):893-902.

Shirahashi et al., Differentiation of human and mouse embryonic stem cells along a hepatocyte lineage. Cell Transplant. 2004;13(3):197-211.

Silván et al., Hypoxia and pluripotency in embryonic and embryonal carcinoma stem cell biology. Differentiation. Sep.-Oct. 2009;78(2-3):159-68. Epub Jul. 14, 2009.

Soto-Gutierrez et al., Differentiation of human embryonic stem cells to hepatocytes using deleted variant of HGF and poly-amino-urethane-coated nonwoven polytetrafluoroethylene fabric. Cell Transplant. 2006;15(4):335-41.

Spagnoli et al., Guiding embryonic stem cells towards differentiation: lessons from molecular embryology. Curr Opin Genet Dev. Oct. 2006;16(5):469-75. Epub Aug. 17, 2006.

Tian et al., Hematopoietic engraftment of human embryonic stem cell-derived cells is regulated by recipient innate immunity. Stem Cells. May 2006;24(5):1370-80. Epub Feb. 2, 2006.

Twork et al., Sensors in Bioprocess Conrol. CRC Press. May 25, 1990. p. 263. Retrieved from https://books.google.com/books?hl=en&lr=&id=9tsUypi4uP4C&oi=fnd&pg=PR3&dq=Twork,+CRC+Press+(1990).+Sensors+in+Bioprocess+Control&ots=PiBP61Bbtg&sig+w1O__9OFpYiUc-P6XQrNB86fcYBo#v=onepage&q=263Twork%2C%2OCRC%20Press%20(1990).%20Sensors%20in%20Bioprocess%20Control&f=false. 1 page.

Van Hoof et al., Differentiation of human embryonic stem cells into pancreatic endoderm in patterned size-controlled clusters. Stem Cell Res. 2011;6:276-85.

Volkmer et al., Hypoxia in static and dynamic 3D culture systems for tissue engineering of bone. Tissue Eng Part A. Aug. 2008;14(8):1331-40. doi: 10.1089/ten.tea.2007.0231.

West et al., In vitro gametogenesis from embryonic stem cells. Curr Opin Cell Biol. Dec. 2004;16(6):688-92.

Wion et al., pO$_2$ matters in stem cell culture. Cell Stem Cell. Sep. 4, 2009;5(3):242-3.

Wolff et al., Microelectrode measurements of pericellular pO$_2$ in erythropoietin-producing human hepatoma cell cultures. Am J Physiol. Nov. 1993;265(5 Pt 1):C1266-70.

Xu et al., Basic FGF and suppression of BMP signaling sustain undifferentiated proliferation of human ES cells. Nat Methods. Mar. 2005;2(3):185-90. Epub Feb. 17, 2005.

Xu et al., BMP4 initiates human embryonic stem cell differentiation to trophoblast. Nat Biotechnol. Dec. 2002;20(12):1261-4. Epub Nov. 11, 2002.

Yoon et al., Enhanced differentiation of human embryonic stem cells into cardiomyocytes by combining hanging drop culture and 5-azacytidine treatment. Differentiation. Apr. 2006;74(4):149-59. Erratum in: Differentiation. Jul. 2006;74(6):322.

Yoshida et al., Hypoxia enhances the generation of induced pluripotent stem cells. Cell Stem Cell. Sep. 2009;5(3):237-41. Epub Aug. 27, 2009.

Zandstra et al., Scalable production of embryonic stem cell-derived cardiomyocytes. Tissue Eng. Aug. 2003;9(4):767-78.

Zhou et al., A gene regulatory network in mouse embryonic stem cells. Proc Natl Acad Sci U S A. Oct. 16, 2007;104(42):16438-43. Epub Oct. 10, 2007.

Cheng et al., Self-renewing endodermal progenitor lines generated from human pluripotent stem cells. Cell Stem Cell. Apr. 6, 2012;10(4):371-84. doi: 10.1016/j.stem.2012.02.024. Supplementary Information.

(56) References Cited

OTHER PUBLICATIONS

Gordon et al., Role of transforming growth factor-beta superfamily signaling pathways in human disease. Biochim Biophys Acta. Apr. 2008;1782(4):197-228. doi: 10.1016/j.bbadis.2008.01.006. Epub Feb. 11, 2008.

Green et al., Generation of anterior foregut endoderm from human embryonic and induced pluripotent stem cells. Nat Biotechnol. Mar. 2011;29(3):267-72. doi: 10.1038/nbt.1788. Epub Feb. 27, 2011.

Nostro et al., Stage-specific signaling through TGFβ family members and WNT regulates patterning and pancreatic specification of human pluripotent stem cells. Development. Mar. 2011;138(5):861-71. doi: 10.1242/dev.055236. Epub Jan. 26, 2011. Erratum in: Development. Mar. 2011;138(5).doi: 10.1242/dev.065904. Development. Apr. 2011;138(7):1445.

Simoni et al., Retinoic acid and analogs as potent inducers of differentiation and apoptosis. New promising chemopreventive and chemotherapeutic agents in oncology. Pure Appl Chem. 2001;73(9):1437-1444.

\* cited by examiner

ARTICLES AND METHODS FOR STEM CELL DIFFERENTIATION

RELATED APPLICATIONS

This application claims priority under 35 U.S.C. §119(e) to U.S. Provisional Patent Application Ser. No. 61/835,326, filed Jun. 14, 2013, and entitled "Template for Stem Cell Growth and Related Methods," which is incorporated herein by reference in its entirety for all purposes.

GOVERNMENT SPONSORSHIP

This invention was made with Government support under Grant No. DE020761, awarded by the National Institutes of Health. The Government has certain rights in this invention.

TECHNICAL FIELD

Articles and methods for stem cell differentiation are generally described.

BACKGROUND

Pluripotent stem cells, including embryonic stem cells and induced pluripotent stem cells are capable of differentiating into all somatic cells of the body. The differentiated cells have potential for major advances in human health. For example, the cells can be used as targets for studying the effects of drugs on specific cells, as models of human disease that can be studied in vitro, and/or to provide a potentially limitless supply for cell therapies for diseases. Many problems stand in the way of achieving the envisioned potential of stem cells. Both embryonic stem cells and induced pluripotent stem cells are difficult to grow and culture while keeping them in the undifferentiated state. In addition, the factors that dictate stem differentiation are not well understood and control of differentiation of stem cells into specific cell lineages and in sufficient quantities remains an obstacle. Accordingly, improved articles and methods for stem cell differentiation are needed.

SUMMARY

Articles and methods for stem cell differentiation are provided. The subject matter of the present invention involves, in some cases, interrelated products, alternative solutions to a particular problem, and/or a plurality of different uses of one or more systems and/or articles.

In one set of embodiments, articles are provided. In one embodiment, an article, comprises a culture vessel for use in stem cells differentiation having a portion comprising an oxygen permeable substrate having at least a portion of a surface coated with a synthetic matrix having an average thickness of less than 100 nm, wherein at least a portion of a surface of the synthetic matrix is covalently bound to biological molecules.

In another embodiment, an article for use in stem cells differentiation comprises an oxygen permeable substrate having at least a portion of a surface coated with a synthetic matrix having an average thickness of less than 90 nm, wherein a surface of the synthetic matrix is covalently bound to biological molecules.

In one set of embodiments, methods are provided. In one embodiment, a method comprises directing the differentiation of stem cells on an oxygen permeable substrate having at least a portion of a surface coated with a synthetic matrix having an average thickness of less than 100 nm, wherein at least a portion of a surface of the synthetic matrix is covalently bound to biological molecules.

In another embodiment, a method comprises directing the differentiation of stem cells on an oxygen permeable substrate having at least a portion of a surface coated with a matrix supporting a cell-supporting protein and essentially free of non-human protein, at least a portion of the cell-supporting protein covalently bound to the matrix.

In yet another embodiment, a method comprises directing the differentiation of stem cells on an oxygen permeable substrate having at least a portion of a surface coated with a matrix formed via an iCVD process.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
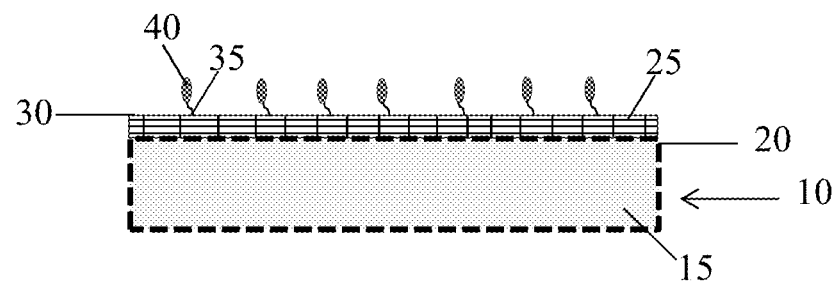
FIGS. 1A-B show a schematic illustration of (A) an article and (B) a culture vessel, according to certain embodiments.

Articles and methods for stem cell differentiation are generally described. In some embodiments, an article (e.g., culture vessel) for stem cell differentiation may comprise an oxygen permeable substrate having at least a portion of a surface coated with a matrix (e.g., synthetic matrix). The matrix may allow the surface chemistry of the substrate to be altered, such that the cell-substrate surface interactions may be finely controlled without substantially affecting the oxygen permeability of the substrate. The surface chemistry may be altered to promote directed stem cell differentiation by, e.g., modification of the matrix surface with a specific density of biological molecules (e.g., extracellular matrix components, proteins, peptides). In some embodiments, methods for stem cell differentiation may comprise directing the differentiation of stem cells (e.g., embryonic stem cells, induce pluripotent stem cells) on the articles, described herein, under suitable environmental conditions (e.g., concentration of soluble factors, partial pressure of oxygen). Articles and methods, described herein, may be free of xenogeneic components (e.g., non-human biologics) and particularly well-suited for applications involving the differentiation of human stem cells into specific lineages (e.g., beta cells).

Pluripotent stem cells (e.g., human embryonic stem cells, human induced pluripotent stem cells) are attractive candidates for numerous cellular and tissue based diagnostics and therapies due to the ability of these cells to differentiate into any somatic cell and the ability of these cells to self-renew. However, reproducible and efficient in vitro directed differentiation of pluripotent stem cells into a desired lineage, as well as maintenance in the undifferentiated self-renewal state, remains an obstacle. It has been hypothesized that in vivo differentiation and maintenance are a complex function of soluble factors, partial pressure of oxygen, and cell-substrate surface interactions, amongst other factors. The role of each factor and the delicate balance that allows for directed differentiation under one set of conditions and maintenance under another remains largely unknown.

Due to the biological complexity of in vivo stem cell differentiation and maintenance, most conventional articles for stem cell culture do not mimic natural stem cell microenvironments and/or development processes. Moreover, many conventional culture articles and methods utilize xenogeneic components (e.g., proteins, cells) that may limit the utility of the resulting cells. For example, the most common conventional techniques are designed to control cell-substrate surface interactions by culturing stem cells on mouse embryonic fibroblast layers or Matrigel, a commercially available gelatinous protein mixture secreted by mouse tumor cells. Both of these techniques introduce xenogeneic proteins (and possibly xenopathogens) of unknown composition, and do not allow for reproducible cell-substrate surface interactions since the composition of the Matrigel and the fibroblast layers may vary from lot to lot. Other techniques control the partial pressure of oxygen experienced by stem cells at the cell-substrate surface interface, but do not allow for the control of cell-substrate surface interactions. Accordingly, improved articles and methods for in vitro stem cell differentiation and/or maintenance are needed.

It has been discovered, within the context of certain embodiments of the present invention, that an oxygen permeable substrate having at least a portion of one surface coated with stable nanoscale matrix that is functionalized to have a desired surface chemistry can be used to better mimic natural stem cell microenvironments and/or development processes. The articles and methods of the present invention may allow for the oxygen partial pressure at the cell-substrate surface interface, cell-substrate surface interactions, and presence or absence of certain soluble factors to be controlled. Surprisingly, it has also been found, within the context of certain embodiments, that by altering certain structural properties (e.g., density of biological molecules) of the article, the article can be changed from promoting directed differentiation to inhibiting differentiation and maintaining pluripotency. Accordingly, in some embodiments, articles suitable for maintenance of stem cells are not suitable for stem cell differentiation. In certain embodiments, articles may be suitable for stem cell differentiation and maintenance.

A non-limiting example of an article (e.g., culture vessel) for directed stem cell differentiation is shown in FIG. 1A. In some embodiments, an article 10 comprises an oxygen permeable substrate 15 having at least a portion of a surface 20 coated with a matrix 25. In some embodiments, the article, the oxygen permeable substrate, and/or the matrix may be essentially free of xenogeneic material (e.g., non-human proteins). In certain embodiments, as illustrated in FIG. 1A, the matrix may be relatively thin (e.g., average thickness of less than 90 nm) and have a surface 30 designed to interact with stem cells. The surface 30 of the matrix may comprise functional groups that can undergo a chemical reaction with biological molecules 40 (e.g., protein) to form covalent bonds 35. In some embodiments, the covalent attachment of biological molecules allows for the cell-substrate surface interactions to be well-defined and promotes directed differentiation.

Figure 1B:
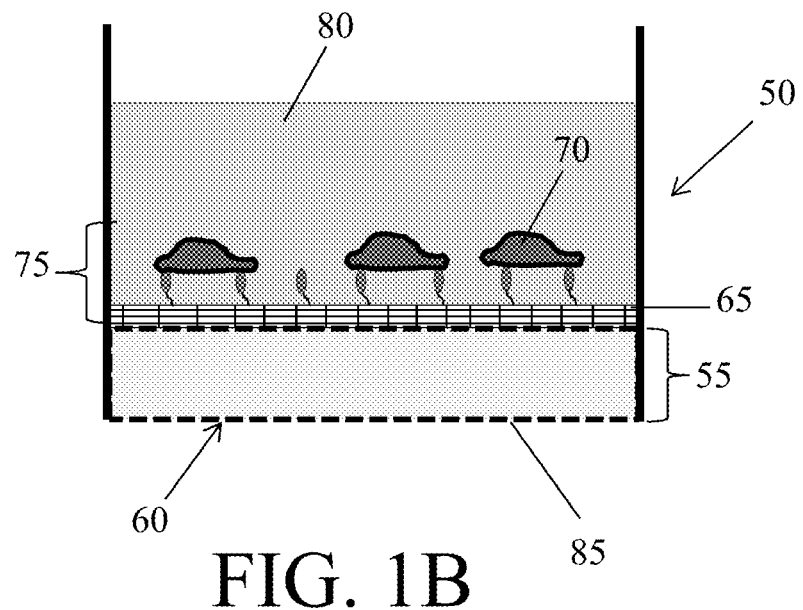

In some embodiments, as illustrated in FIG. 1B, the article is a culture vessel 50. At least a portion of the culture vessel may be defined by the coated oxygen permeable substrate 55, described in more detail below. In certain embodiments, at least a portion of the bottom 60 of the culture vessel is defined by the coated oxygen permeable substrate as illustrated in FIG. 1B. In some such embodiments, the coated surface 65 of the substrate is used for cell culture. The coated surface and the biological cells 70 form the cell-substrate surface interface 75 and the biological molecules attached to the surface may dictate at least a portion of the interaction between the cells and the substrate surface. In some embodiments, the culture vessel may be used for liquid cell culture. During use, at least a portion of the vessel may be filled with cell culture medium 80. In some embodiments, the culture vessel is optionally part of a culture system. In some such cases, hardware for supplying a known concentration of oxygen (referred to herein as an oxygen source) may be in fluid communication with the coated oxygen surface, e.g., such that oxygen enters the substrate through the surface facing the away from the culture medium and/or cells (e.g., surface 85). Those of ordinary skill in the art would be aware of suitable oxygen sources.

It should be understood that FIG. 1B is a non-limiting schematic of a culture vessel and other configurations are possible. For example, in certain embodiments, at least a portion of the bottom of the culture vessel is not be defined by the coated oxygen permeable substrate. In some such cases, at least a portion of one or more sides or walls of the culture vessel may be defined by the coated oxygen permeable substrate. In other embodiments, at least a portion of one or more sides or walls of the culture vessel, in addition to the bottom, is defined by the coated oxygen permeable substrate.

As described herein, an article for stem cell differentiation comprises a matrix coating at least a portion of the oxygen permeable substrate. The matrix may modify the surface chemistry of the oxygen permeable substrate and allows for the facile, controlled, and stable attachment of biological molecules to the surface without adversely affecting the oxygen permeability of the substrate and/or the article. In some embodiments, the matrix comprises a plurality of functional groups on and/or near its surface. The density of the functional groups on the surface may be controlled during the coating process (e.g., an initiated chemical vapor deposition process), such that a matrix having a specific density of functional groups is formed. The functional groups may be modified using a chemical reaction to covalently attach the biological molecules to the surface. In some embodiments, the density of the biological molecules on the surface is limited by the density of functional groups on the matrix surface. In such embodiments, the density of biological molecules on the surface may be controlled by the matrix.

Moreover, it has surprisingly been found, in the context of certain embodiments of the present invention, that the density of certain covalently attached biological molecules can be used to promote or inhibit directed differentiation of stem cells. It has also been surprisingly found, in the context of certain embodiments of the present invention, that biological molecule surface densities having similar stem cell maintenance properties can have different properties with respect to stem cell differentiation. For example, certain densities of biological molecules that allow for stem cell attachment and/or maintenance do not allow for directed differentiation. In some such embodiments, the ability of the stem cells to attach and/or be maintained on a surface is not a sufficient indication of the suitability of the surface for directed differentiation.

As mentioned above, the biological molecules may have a certain density on the matrix surface. The density of the biological molecules on the surface may be quantified by determining the percentage of bonds associated with the covalent linkage between the matrix and the biological molecules using quantitative ATR-FTIR. Those of ordinary skill in the art would be knowledge of quantitative ATR-FTIR techniques (e.g., in combination with Beer-Lambert's law) used to determine the concentration of a group and/or percentage of a group on the surface. For example, the percentage of the covalent bond to the biological molecules in the matrix surface may be determined in a similar manner as described in the Coclite, et al. Plasma Process. Polym. 2101, 9, 425-434 and Example 3. Briefly, the percentage of the area ratio of the fitted peak area (i.e., the area under the peak determined using standard fitting methods) of the covalent bond between the matrix and the biological molecules to the sum of the fitted peak areas of all the groups in the spectrum, including the bond between the matrix and the biological molecules, may be used. In some embodiments, the percentage of the matrix surface has a covalent bond to the biological molecules is between about 25% and about 80%, between about 25% and about 75%, between about 25% and about 70%, between about 25% and about 65%, between about 25% and about 60%, between about 25% and about 54%, between about 30% and about 80%, between about 30% and about 75%, between about 30% and about 70%, between about 30% and about 65%, or between about 30% and about 60%. In certain embodiments, the percentage suitable for directed stem cell differentiation is between about 30% and about 54% (e.g., between about 30% and about 50%, between about 30% and about 45%, between about 30% and about 40%). In some such embodiments, percentages greater than about 54% inhibits or prevents directed differentiation and less than about 54% (e.g., less than or equal to about 50%, less than or equal to about 45%) promotes directed differentiation.

It should be understood that the suitable percentages of matrix surface has a covalent bond to the biological molecules may vary based on the stem cell type and the desired differentiated cell lineage. Other values are possible.

As mentioned above, the matrix may be relatively thin (e.g., less than or equal to 100 nm, less than 90 nm). In some embodiments, the average thickness of the matrix may be less than or equal to about 100 nm, less than or equal to about 90 nm, less than or equal to about 80 nm, less than or equal to about 70 nm, less than or equal to about 60 nm, less than or equal to about 50 nm, less than or equal to about 40 nm, less than or equal to about 30 nm, or less than or equal to about 20 nm. In some instances, the average thickness of the matrix is between about 10 nm and about 100 nm, between about 10 nm and about 90 nm, between about 10 nm and about 80 nm, between about 10 nm and about 70 nm, between about 10 nm and about 60 nm, or between about 10 nm and about 50 nm. In some embodiments, the average thickness may be determined in the dry state as described in Petruczok, et al. Macromolecules, 2013, 46 (5), 1832-1840. Other methods for determining thickness in the dry state include profilometry, scanning electron microscopy, and atomic force microscopy. Those of ordinary skill in the art would be aware of suitable techniques for determining the thickness of a matrix in the dry state.

Without being bound by theory, it is believed that the permeability of coating is dependent on the inherent permeability of the matrix material and the thickness of the matrix. The matrix material and thickness may be selected such that the oxygen permeability of the substrate is not significantly reduced. However, even for matrix materials with relatively high oxygen permeability, certain matrix thicknesses may significantly reduce the oxygen permeability of the substrate, such that the partial pressure of oxygen at the cell-substrate surface interface is reduced. In some embodiments, the thickness of the matrix and/or the matrix material is selected to minimize or eliminate the reduction in oxygen permeability due to the presence of the matrix. For instance, in some embodiments, the oxygen permeability of the coated oxygen permeable substrate may be at least about 50%, at least about 60%, at least about 70%, least about 75%, at least about 80%, at least about 85%, least about 90%, at least about 95%, at least about 97%, or at least about 99% of the oxygen permeability of the uncoated oxygen permeable substrate as determined using the permeability divided by thickness as the measure of permeability. In certain embodiments, coated oxygen permeable substrates having thicker coatings and lower diffusivities can be used for stem cell maintenance, whereas coated oxygen permeable substrates having thinner coatings and higher diffusivities are used for directed differentiation.

In some embodiments, the matrix is not covalently bond to the substrate as illustrated in FIG. 1. In other embodiments, the matrix may be attached to the surface via covalent bonds. In some embodiments, the matrix may be coated onto the surface of the substrate using a deposition process. Those of ordinary skill in the art are knowledgeable of deposition process for coating substrates. Non-limiting examples of deposition processes include chemical vapor deposition (CVD), physical vapor deposition, spin coating, layer by layer assembly, and Langmuir-Blodglett film deposition methods. In certain embodiments, the matrix may be formed and deposited on the surface using an initiated chemical vapor deposition (iCVD). iCVD techniques are known to those of ordinary skill in the art and are described in the literature, for example, see, Tenhaeff et al., Adv. Funct. Mater. 18, 979-992 (2008); and S. H. Baxamusa, S. G. Im, K. K. Gleason, Phys. Chem. Chem. Phys. 11, 5227 (2009), each herein incorporated by reference. As will be known to those of ordinary skill in the art, iCVD, is a solvent-free, vacuum-based technique, in which polymer matrices are formed directly on the substrate by free radical polymerization of vapor-phase monomer at low temperature (25-150° C.) and under moderate vacuum (~0.2 Torr). In iCVD, monomer and initiator flow into a vacuum chamber where they contact resistively heated filaments. The initiator breaks down into radicals, beginning a free-radical polymerization of the monomer at the substrate surface. Crosslinking monomers may be used in iCVD processes to form a crosslinked polymer matrix. In some instances, the crosslinked polymer matrices may have enhanced stability compared to essentially identical matrices that are not crosslinked. Moreover, iCVD may be used to form and deposit a wide variety of polymer, including polymers comprising functional groups. iCVD is compatible with a wide variety of substrates and is capable of producing uniform, continuous coatings, that are conformal on the nanoscale, over large areas. One advantage of iCVD, used herein, is the ability to modify a wide variety of substrates without the need for a pretreatment step (e.g., a chemical pretreatment step). In many conventional surface modification techniques, the substrate surface must be treated to have the appropriate moieties (e.g., functional groups) on the substrate surface prior to modification.

Another advantage of iCVD, used herein, is the ability to easily and systematically tune the properties of the resulting polymer matrix by altering the composition of the feed gas comprising the monomers. For example, the density of certain functional groups on the surface of the matrix may be changed by changing the ratio of different components (e.g., monomers) in the feed gas. In some such embodiments, the feed gas is changed such that the concentration of monomers having the desired functional is altered. In some instances, higher concentrations of the monomer having the desired functional groups in the feed gas results in a matrix having a higher concentration of the functional group on the matrix surface. As another example, compositional gradient within the depth of the matrix may be formed by changing the feed gas ratios during the deposition. For instance, a matrix may be formed such that the majority of the functional groups are at or near the surface of the matrix. The confinement of the functional groups at or near the surface allows for substantially all of the functional groups to be accessible, even to large functionalizing agents. Conversely, in another example, a matrix may be formed such that a portion of the functional groups are away from the surface and toward the interior of the matrix, making some functional groups inaccessible.

In some embodiments, the use of a matrix may increase the stability and/or shelf life of the article (e.g., culture vessel). For instance, in some embodiments, articles comprising an oxygen permeable substrate coated with a matrix having biological molecules covalently attached thereto have enhanced stability and/or a greater shelf life at 4° C. compared to articles comprising an oxygen permeable substrate having biological molecules non-covalently (e.g., physically absorbed) to the substrate surface. In some such embodiments, the articles comprising an oxygen permeable substrate coated with a matrix having biological molecules covalently attached to the matrix have a shelf life at 4° C. of greater than or equal to 1 weeks, greater than or equal to 2 weeks, greater than or equal to 2.5 weeks, greater than or equal to 3 weeks, greater than or equal to 3.5 weeks, greater than or equal to 4 weeks, greater than or equal to 4.5 weeks, greater than or equal to 5 weeks, greater than or equal to 5.5 weeks, greater than or equal to 6 weeks, greater than or equal to 7 weeks, or greater than or equal to 8 weeks. In some embodiments, the shelf life at 4° C. may be between about 1 weeks and about 8 weeks, between about 1 weeks and about 6 weeks, or between about 2 weeks and about 6 weeks.

As used herein, the terms "shelf life" refers to the length of time the article can be stored, e.g. at 4° C. as noted above, without the elemental composition, as determined by X-ray photoelectron spectroscopy or quantitative ATR-FTIR, of the functionalized surface changing significantly. A significant change in elemental composition refers to a change in the percentage of any one element (e.g., carbon, oxygen, nitrogen, silicon) as determined by XPS by 5%, change in the percentage of any one element from a positive non-zero integer to zero as determined by XPS, or the change in the percentage of covalently bonded biological molecules as determined by quantitative ATR-FTIR, as described herein. In some embodiments, the shelf life may be determined using quantitative ATR-FTIR. In some embodiments, the coating and/or attached biological molecules may be relatively stable, such that the coating and/or attached biological molecules do not physically (e.g., delaminate) and/or chemically separate from the substrate during storage and/or use. In some embodiments, the stability of the article allows the article to withstand sterilization processes (e.g., ethanol and/or UV treatments).

It should be understood that whether a product actually is or is not stored at 4° C. in use may be irrelevant to whether the product meets the shelf life criteria noted above. For example, although a product might be stored at a temperature different than 4° C. in use, if that product is to be evaluated as to whether it meets this shelf life criteria than it is stored at 4° C. for the time indicated and measurement as to change in elemental composition is made.

In some embodiments, the matrix may serve to alter or enhance the wettability of the substrate surface. In certain embodiments, the change in wettability of the substrate surface may enhance stem cell attachment and/or differentiation. In some embodiments, the change in the wettability of the substrate surface may be due to the matrix composition alone or in combination with the covalent attached biological molecules. In some embodiments, the matrix may decrease the water contact angle of the substrate surface. For example, a hydrophilic matrix may be deposited on a relatively hydrophobic substrate. In some embodiments, the coated substrate surface may have a water contact angle of less than or equal to about 100 degrees, less than or equal to about 90 degrees, less than or equal to about 80 degrees, less than or equal to about 70 degrees, less than or equal to about 60 degrees, less than or equal to about 50 degrees, less than or equal to about 40 degrees, or less than or equal to about 30 degrees. In some instances, the coated substrate surface may have a water contact angle of between about 30 degrees and about 90 degrees, between about 30 degrees and about 85 degrees, between about 30 degrees and about 80 degrees, between about 30 degrees and about 75 degrees, between about 45 degrees and about 75, or between about 60 degrees and about 75 degrees.

As described herein, biological molecules may be covalently attached to the matrix. In general, the linkage between the matrix and the biological molecule may comprise any suitable bond that is relatively stable under stem cell culture conditions and/or is readily formed between the matrix and biological molecules. Non-limiting examples of suitable bonds include amide bonds, ester bonds, and ether bonds. As used herein, the term "biological molecule" refers to a molecule that comprises at least one of sugar, amino acid, nucleotide, or fatty acid. The biological molecules may be composed of natural or non-natural sugars, amino acids, nucleotides, or fatty acids. In certain embodiments, the biological molecule is a macromolecule comprising sugar, amino acid, nucleotide, and/or fatty acid repeat units. In some embodiments, the biological molecule may be capable of undergoing a biological binding event (e.g, between complementary pairs of biological molecules) with another biological molecule.

Exemplary biological molecules include, but are not limited to, proteins (e.g., extracellular matrix proteins, antibodies, receptors), nucleic acids, glycoproteins, lipids, and carbohydrates (e.g., maltose), and derivatives or fragments thereof. In some embodiments, the biological molecule is a cell-supporting protein. A cell supporting protein has its ordinary meaning in the art and may refer to a protein capable of facilitating and/or promoting biological cell attachment, proliferation, maintenance, and/or differentiation. In some embodiments, the biological molecule is an extracellular matrix component, such as fibronectin, collagen, fibrin, or heparan sulfate proteoglycans. In some embodiments, regardless of the type of biological molecule attached to the surface, the biological molecule may be non-xenogeneic (e.g., human biological molecule). Biological molecules suitable for use in the embodiments described herein can be selected readily, by those of ordinary skill in the art, based upon the description herein as their function and the provided examples of such biological molecules. It should be understood that two or more different biological molecules may be covalently attached to the matrix surface. However, in some embodiments, a single type of biological molecule is attached to the matrix surface.

As described herein, the article for stem cell differentiation may comprise an oxygen permeable substrate. As used herein, an "oxygen permeable substrate" refers to a material having an oxygen permeability divided by thickness of the substrate of greater than $0.1\times10^{-14}$ mol $sec^{-1}$ $cm^{-2}$ mm $Hg^{-1}$ at 37° C. Those of ordinary skill in the art would be knowledge of methods to measure oxygen permeability divided by thickness of the substrate (referred to herein as oxygen permeability/thickness). Without being bound by theory, it is believed that when a culture vessel has at least a portion of one or more sides, walls, and/or bottom comprising an oxygen permeable substrate, the partial pressure of oxygen at the cell-substrate surface interface (i.e., $pO_{2cell}$) can be finely controlled.

In typical cell culture, oxygen levels are controlled by placing culture vessels in humidified incubators with a defined gas phase partial pressure of oxygen. The oxygen partial pressure in the gas phase of a culture system is referred to herein as $pO_{2gas}$. Since the cells are in a liquid cell culture medium, the cells consume oxygen supplied by diffusion. When cells are cultured in culture vessels consisting of non-oxygen permeable substrates or substrates with relatively low oxygen permeability, the difference between the $pO_{2gas}$ and $pO_{2cell}$ is relatively high. Moreover, since the oxygen partial pressure experienced by the cells depend on several factors including culture medium depth, cell density, cellular oxygen consumption rate, diffusion characteristics of the cell culture medium, and $pO_{2gas}$, the $pO_{2cell}$ is difficult to control in culture vessels consisting of non-oxygen permeable substrates or substrates with relatively low oxygen permeability. Culture vessels including at least a portion of one or more sides, walls, and/or bottom comprising an oxygen permeable substrate can reduce and or eliminate the difference between the $pO_{2gas}$ and the $pO_{2cell}$. In some embodiments, $pO_{2gas}$ may be substantially the same $pO_{cell}$ in culture vessels having at least a portion of one or more walls, sides, and/or bottom defined by an oxygen permeable substrate. In some cases, $pO_{2gas}$ may be substantially the same $pO_{2cell}$ in culture vessels having a bottom comprising an oxygen permeable substrate.

In some embodiments, the oxygen permeability/thickness of the oxygen permeable substrate, coated oxygen permeable substrate, and/or the article may be relatively high. For instance, in some embodiments, the oxygen permeability/thickness of the oxygen permeable substrate, coated oxygen permeable substrate, and/or the article at 37° C. may be greater than or equal to about $0.1\times10^{-14}$ mol $sec^{-1}$ $cm^{-2}$ mm $Hg^{-1}$, greater than or equal to about $0.2\times10^{-14}$ mol $sec^{-1}$ $cm^{-2}$ mm $Hg^{-1}$, greater than or equal to about $0.5\times10^{-14}$ mol $sec^{-1}$ $cm^{-2}$ mm $Hg^{-1}$, greater than or equal to about $1\times10^{-14}$ mol $sec^{-1}$ $cm^{-2}$ mm $Hg^{-1}$, greater than or equal to about $5\times10^{-14}$ mol $sec^{-1}$ $cm^{-2}$ mm $Hg^{-1}$, greater than or equal to about $10\times10^{-14}$ mol $sec^{-1}$ $cm^{-2}$ mm $Hg^{-1}$, greater than or equal to about $25\times10^{-14}$ mol $sec^{-1}$ $cm^{-2}$ mm $Hg^{-1}$, greater than or equal to about $50\times10^{-14}$ mol $sec^{-1}$ $cm^{-2}$ mm $Hg^{-1}$, greater than or equal to about $75\times10^{-14}$ mol $sec^{-1}$ $cm^{-2}$ mm $Hg^{-1}$, greater than or equal to about $100\times10^{-14}$ mol $sec^{-1}$ $cm^{-2}$ mm $Hg^{-1}$, greater than or equal to about $250\times10^{-14}$ mol $sec^{-1}$ $cm^{-2}$ mm $Hg^{-1}$, greater than or equal to about $500\times10^{-14}$ mol $sec^{-1}$ $cm^{-2}$ mm $Hg^{-1}$, greater than or equal to about $750\times10^{-14}$ mol $sec^{-1}$ $cm^{-2}$ mm $Hg^{-1}$, greater than or equal to about $1,000\times10^{-14}$ mol $sec^{-1}$ $cm^{-2}$ mm $Hg^{-1}$, greater than or equal to about $1,250\times10^{-14}$ mol $sec^{-1}$ $cm^{-2}$ mm $Hg^{-1}$, greater than or equal to about $1,500\times10^{-14}$ mol $sec^{-1}$ $cm^{-2}$ mm $Hg^{-1}$, greater than or equal to about $1,750\times10^{-14}$ mol $sec^{-1}$ $cm^{-2}$ mm $Hg^{-1}$, or greater than or equal to about $2,000\times10^{-14}$ mol $sec^{-1}$ $cm^{-2}$ mm $Hg^{-1}$.

In some embodiments, the oxygen permeability/thickness of the oxygen permeable substrate, coated oxygen permeable substrate, and/or the article at 37° C. is between about $0.1\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $75\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $150\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $250\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $500\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $750\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $1,000\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, or between about $1,500\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$.

In some embodiments, the oxygen permeability/thickness used for stem cell differentiation may be between about $500\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $750\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, between about $1,000\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$, or between about $1,500\times10^{-14}$ mol $sec^{-1}$ $cm^{-2}$ mm $Hg^{-1}$ and about $3,500\times10^{-14}$ mol $sec^{-1}$ $cm^{-2}$ mm $Hg^{-1}$.

In some embodiments, the oxygen transmission rate of the oxygen permeable substrate, coated oxygen permeable substrate, and/or the article may be relatively high. For instance, in some embodiments, the oxygen transmission rate of the oxygen permeable substrate, coated oxygen permeable substrate, and/or the article may be greater than or equal to about 0.00067 $cm^3/cm^2$/day/atm, greater than or equal to about 0.001 $cm^3/cm^2$/day/atm, greater than or equal to about 0.005 $cm^3/cm^2$/day/atm, greater than or equal to about 0.01 cm³/cm²/day/atm, greater than or equal to about 0.05 cm³/cm²/day/atm, greater than or equal to about 0.1 cm³/cm²/day/atm, greater than or equal to about 0.2 cm³/cm²/day/atm, greater than or equal to about 0.5 cm³/cm²/day/atm, greater than or equal to about 1 cm³/cm²/day/atm, greater than or equal to about 2 cm³/cm²/day/atm, greater than or equal to about 5 cm³/cm²/day/atm, greater than or equal to about 8 cm³/cm²/day/atm, greater than or equal to about 10 cm³/cm²/day/atm, greater than or equal to about 0.00067 cm³/cm²/day/atm, greater than or equal to about 12 cm³/cm²/day/atm, or greater than or equal to about 15 cm³/cm²/day/atm.

In some embodiments, the oxygen transmission rate of the oxygen permeable substrate, coated oxygen permeable substrate, and/or the article may be between about 0.00067 cm³/cm²/day/atm and about 25 cm³/cm²/day/atm, between about 0.01 cm³/cm²/day/atm and about 25 cm³/cm²/day/atm, between about 0.1 cm³/cm²/day/atm and about 25 cm³/cm²/day/atm, between about 1 cm³/cm²/day/atm and about 25 cm³/cm²/day/atm, or between about 5 cm³/cm²/day/atm and about 25 cm³/cm²/day/atm. In some embodiments, the used for stem cell differentiation may be between 5 cm³/cm²/day/atm and about 25 cm³/cm²/day/atm.

In general, the oxygen permeable substrate may be any suitable xenogeneic free material having the requisite oxygen permeability/thickness. Those of ordinary skill in the art would be aware of suitable material based on the description provided herein. In some embodiments, the oxygen permeable substrate comprises synthetic material. In some such embodiments, the oxygen permeable substrate consists essentially of synthetic materials. Non-limiting examples of suitable materials include silicon rubber, silicone-polycarbonate, and fluoropolymers (e.g., fluorinated ethylene-propylene copolymer). In some embodiments, the oxygen permeable substrate is silicon rubber.

It should be understood that though the matrix having covalently bond biological molecules has been described as coating an oxygen permeable substrate, in certain embodiments, the matrix having the features (e.g., composition, biological molecule density), described herein, may be used on a non-oxygen permeable substrate (e.g., polystyrene).

In one aspect of the invention, methods for directing stem cell differentiation are provided. As used herein, the phrase "directing stem cell differentiation" and "directed differentiation" has its ordinary meaning in the art and may refer to a differentiation process that is non-spontaneous and is controllably induced by one or more features of articles or methods used for differentiation. A method for directed differentiation may comprise directing the differentiation of stem cells to a particular lineage on the articles, described herein. In one example, the method includes directing the differentiation of stem cells on an oxygen permeable substrate having at least a portion of a surface coated with a matrix (e.g., formed via an iCVD process), described herein. The matrix (e.g., synthetic matrix) may have an average thickness of less than 100 nm (e.g., less than 90 nm) and at least a portion of the matrix surface is covalently bound to biological molecules, such as proteins. In another example, the method includes directing differentiation of stem cells on an oxygen permeable substrate having at least a portion of a surface coated with a matrix, described herein. The matrix may support a cell-supporting protein and may be essentially free of xenogeneic proteins (e.g., non-human protein). In some instances, at least a portion of the cell-supporting protein is covalently bound to the matrix.

In some embodiments, the directed differentiation method comprises exposing the stem cells to certain soluble factors and/or controlling or altering the $pO_{2cell}$ during the differentiation process. Non-limiting examples of directed differentiation methods comprising controlling oxygen are described in U.S. Publication No. 2013/0287743 filed Apr. 29, 2013, entitled "Methods for Differentiating Human Embryonic Stem Cells into β-cells for the Treatment of Type I Diabetes" and having the inventors Colton et al.; U.S. Publication No. 2010/0261277 filed Jun. 13, 2008, entitled "Methods and Compositions for Enhanced Differentiation from Embryonic Stem Cells" and having the inventors Colton et al.; D'Amour et al. Nat. Biotechnol. 24, 1393-1401 (2006); and Hrvatin, et al., "Differentiated human stem cells resemble fetal, not adult, β cells" PNAS 2014, and are incorporated herein by reference in their entirety.

In some embodiments, the directed differentiation method comprises controlling and/or altering the partial pressure of oxygen at the cell-substrate surface interface during the differentiation process. In certain embodiments, the methods includes culturing of pluripotent stem cells at relatively low oxygen partial pressures (e.g., less than about 142 mm Hg, less than or equal to about 50 mm Hg, 7 mm Hg, 36 mm Hg) at least for an initial period. In some embodiments, after culturing the cells at a low partial pressure, the partial pressure of oxygen may be increased (e.g., to greater than or equal to about 142 mm Hg, 142 mm Hg). In other embodiments, the cells remain at low oxygen throughout the entire differentiation period or the oxygen level is decreased during the differentiation period. In some embodiments, the differentiation period is at least 1 day, at least 2 days, at least 3 days, or at least 6 days.

In some embodiments, a two-step differentiation process involves differentiating stem cells (e.g., human stem cells) to a definitive endoderm stage at a low oxygen partial pressure and differentiating the definitive endoderm stage to an immature stage at an increased oxygen partial pressure. In some embodiments, an immature stage refers to cells that are further differentiated down the pathway of the final cell type but are either not the final cell type or are the final cell type but do not have the full responses. For example, an immature beta cell expresses the hormone insulin like mature beta cells, but do not secrete glucose upon glucose simulation. Further maturation is required for the cells to behave like adult (mature) beta cells. In some embodiments in which a two-step differentiation process is used, the first differentiation step is followed by a second differentiation step at a second oxygen partial pressure that is greater than the first oxygen partial pressure. The first oxygen partial pressure may be less than or equal to about 50 mm Hg, less than or equal to about 40 mm Hg, less than or equal to about 30 mm Hg, less than or equal to about 20 mm Hg, less than or equal to about 10 mm Hg, or 0 mm Hg. The first oxygen partial pressure may be between about 30 and about 50 mm Hg, between about 30 and about 40 mm Hg, between about 35 mm Hg and about 50 mm Hg, and between about 35 and about 40 mm Hg, including every integer therebetween. In one particular embodiment, the first oxygen partial pressure is about 7 mm Hg. In another particular embodiment, the first oxygen partial pressure is about 36 mm Hg.

The second oxygen partial pressure may be at least about 80 mm Hg, at least about 100 mm Hg, at least about 120 mm Hg, or at least about 135 mm Hg, at least about 150 mm Hg, at least about 170 mm Hg, or at least about 200 mm Hg. The second oxygen partial pressure may be between about 120 mm Hg and about 150 mm Hg, between about 125 mm Hg and about 150 mm Hg, between about 130 mm Hg and about 150 mm Hg, between about 135 mm Hg and about 150 mm Hg, between about 140 mm Hg and about 150 mm Hg, and between about 140 mm Hg and about 145 mm Hg, including every integer therebetween. In one particular embodiment, the second oxygen partial pressure is about 142 mm Hg. The low oxygen culture step is generally referred to herein as the first culture step regardless of whether oxygen level is later increased, and the higher oxygen culture step is generally referred to herein as the second differentiation step.

In some embodiments the first differentiation step occurs for a first period of time of about 1 day to about 8 days, including every integer therebetween. The first time period may be about 2 days to about 8 days, about 4 days to about 6 days, or about 5 days to about 7 days, including every integer therebetween. In one embodiment, the first time period is 6 days. In this and other embodiments, the second differentiation step occurs for a second period of time of about 1 day to about 20 days, about 2 days to about 20 days, about 5 days to about 20 days, about 10 days to about 20 days, or about 12 days to about 18 days including every integer therebetween. The second time period may be 15 days. In another embodiment, the first time period and the second time period total to at least about 10 days, at least about 15 days, or at least about 20 days. In one embodiment, the first time period and the second time period total to 21 days.

In some embodiments, stem cells differentiated on articles, described herein, may have a relatively high percentage of cells at the desired stage (e.g., specific lineage). For instance, in some embodiments, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% are at the desired stage.

In general, any suitable material having the desired oxygen permeability/thickness properties, that is compatible with the deposition process, and that comprises functional groups or functional group precursors may be used for the coating. In some embodiments, the matrix is or comprises a polymer matrix (e.g., cross-linked, uncross-linked), inorganic matrix, organic matrix, or combinations thereof. In certain embodiments, the matrix may be crosslinked. In some instances, a crosslinked matrix increases the stability and/or shelf life of the article. In other instances, crosslinking does not influence the stability and/or shelf life of the article. In some embodiments, the matrix may be free of xenogeneic material (e.g., non-human material). In some such cases, the matrix may comprise synthetic materials.

In certain embodiments, the matrix is a polymer matrix. For example, the matrix may be a polymer matrix formed via an iCVD process. In some such cases, the polymer matrix may be formed from monomers (e.g., vinyl monomers) comprising functional groups or precursors thereof. Non-limiting examples of suitable monomers include acrylates (e.g., methacrylates, diacrylates, alkylacrylates, alkylmethacrylates, dimethacrylate, methacrylic or acrylic acid), organosilicon, siloxane, styrene and styrene derivate, divinylbenzene, p-divinylbenzene, vinylimidazole, vinyl pyrrolidone, divinyloxybutane, diethylene glycol divinyl ether. In general, any suitable number of monomer may be used in the iCVD process to form the matrix. Monomers can be used alone, or mixtures of different monomers (e.g., two monomers, three monomers, four monomers) can be used to form homopolymers and/or copolymers. For example, the matrix may be formed from three monomers (e.g., three acrylate monomers). In some instances in which multiple monomers are used, at least one monomer is a crosslinking monomer capable of forming crosslinked matrix. In other instances, a crosslinking monomer is not used.

In general, the polymer matrix may comprise any suitable polymer molecules comprising functional groups. Polymer molecules are generally extended molecular structures comprising backbones which optionally contain pendant side groups, wherein the term backbone is given its ordinary meaning as used in the art, e.g., a linear chain of atoms within the polymer molecule by which other chains may be regarded as being pendant. Typically, but not always, the backbone is the longest chain of atoms within the polymer. A polymer may be a co-polymer, for example, a block, alternating, or random co-polymer. A polymer may also comprise a mixture of polymers. In some embodiments, the polymer may be acyclic or cyclic. A polymer may be cross-linked, for example through covalent bonds, ionic bonds, hydrophobic bonds, and/or metal binding. Polymer molecules may be obtained from natural sources or be created synthetically.

An exemplary, non-limiting list of polymer molecules that are potentially suitable for use in the invention includes polysaccharides; polynucleotides; polypeptides; peptide nucleic acids; polyacrylates, polyamides; polyphosphazenes; polyamines; polyesters; polyethers; poly(ether esters) that have functional groups (e.g., pendant functional groups); and derivatives and block, random, radial, linear, or teleblock copolymers, and/or blends of the above. Other potentially suitable polymer molecules are described in the Polymer Handbook, Fourth Ed. Brandrup, J. Immergut, E. H., Grulke, E. A., Eds., Wiley-Interscience: 2003, which is incorporated herein by reference in its entirety.

In some cases, the polymer molecule may form a hydrogel. As used herein, the term hydrogel is given its ordinary meaning as used in the art, e.g., a network of polymer chains in an aqueous dispersion medium. In some embodiments, a hydrogel may comprise a plurality of cross-linked polymer molecules. In some cases, a hydrogel polymer matrix is formed by crosslinking the polymer molecules. Non-limiting examples of polymer molecules capable of forming hydrogels include polysaccharides, polyacrylamides, polyvinyl alcohol, acrylate polymers (e.g., sodium polyacrylate), and copolymers with an abundance of hydrophilic groups. In general, the hydrogel matrix may be formed by cross-linking the polymer molecules. In general, any suitable crosslinking method may be used. For instance, polymer matrix may be covalently crosslinked. Those of ordinary skill in the art would be knowledge of suitable crosslinking methods.

In some embodiments, the polymer molecules may form a gel. As used herein, the term gel is given its ordinary meaning in the art and refers to polymer molecules that may be cross-linked to form a network, wherein the network may be able to trap and contain fluids. Depending on the level of crosslinking, various properties of a particular gel can be tailored. For example, a highly cross-linked gel may generally be structurally strong and may resist releasing fluid under pressure. Those of ordinary skill in the art would be able to identify methods for modulating the degree of crosslinking in such gels.

The polymer molecules may have any suitable molecular weight. For example, in some embodiments, the polymer molecules may have an average molecular weight greater than 1000 Da, in certain embodiments greater than 5000 Da, in certain embodiments greater than 10000 Da, in certain embodiments greater than 20000 Da, in certain embodiments greater than 50000 Da, in certain embodiments greater than 100000 Da, in certain embodiments greater than 500000 Da, or in certain embodiments greater than 1000000

Da. In some embodiments, the polymer molecules may have at least 5 subunits, in certain embodiments at least 10 subunits, in certain embodiments at least 20 subunits, in certain embodiments at least 30 subunits, in certain embodiments at least 50 subunits, in certain embodiments at least 100 subunits, in certain embodiments at least 500 subunits, in certain embodiments at least 1000 subunits, or in certain embodiments at least 5000 subunits.

In general, any suitable percentage of the substrate surface may be coated with the matrix. For instance, in some embodiments, at least about 50%, at least about 55%, at least about 60%, at least about 65%, at least about 70%, at least about 75%, at least about 80%, at least about 85%, at least about 90%, at least about 95%, at least about 97%, or at least about 99% of the substrate surface is coated with the matrix. In certain embodiments, substantially one entire substrate surface is coated with the matrix. In certain embodiments, the coating may be a continuous coating. In some embodiments, the matrix may coat the surface of the substrate without coating at least a portion of the interior of the substrate. For example, the matrix may coat the region of the substrate at or near the substrate surface.

In general, the article (e.g., culture vessel) may have any suitable shape or dimension. In some embodiments, the dimensions of the article may be selected as desired. It should be understood that the article can have any suitable cross-sectional dimension. For instance, in some embodiments, article (e.g., culture vessel) may have a maximum cross-sectional dimension of greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, the article, may have a maximum cross-sectional dimension of less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values of maximum cross-sectional dimensions are also possible.

In some cases, at least one or at least two cross-sectional dimensions (e.g., a height and a width) of article may be greater than or equal to about 0.01 cm, greater than or equal to about 0.05 cm, greater than or equal to about 0.1 cm, greater than or equal to about 1 cm, greater than or equal to about 2 cm, greater than or equal to about 5 cm, greater than or equal to about 10 cm, greater than or equal to about 20 cm, greater than or equal to about 30 cm, greater than or equal to about 40 cm, greater than or equal to about 50 cm, greater than or equal to about 60 cm, greater than or equal to about 70 cm, greater than or equal to about 80 cm, or greater than or equal to about 90 cm. In some instances, at least one or at least two cross-sectional dimensions of article may be less than or equal to about 100 cm, less than or equal to about 90 cm, less than or equal to about 80 cm, less than or equal to about 70 cm, less than or equal to about 60 cm, less than or equal to about 50 cm, less than or equal to about 40 cm, less than or equal to about 30 cm, less than or equal to about 20 cm, less than or equal to about 10 cm, or less than or equal to about 5 cm. Combinations of the above-referenced ranges are also possible (e.g., greater than or equal to about 1 cm and less than or equal to about 100 cm). Other values are also possible.

The article (e.g., culture vessel) may have a certain width-to-height ratio. In certain instances, the ratio of the width to height of article may be greater than or equal to about 1:1, greater than or equal to about 2:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

The article (e.g., culture vessel) may also have an aspect ratio (length to largest average cross-sectional dimension) of at least 2:1, more typically at least 3:1, 8:1, or 20:1. In some cases, the channels, channel segments, or channel portions have very large aspect ratios, e.g., at least 100:1, 500:1 or 1000:1.

In some embodiments, at least a portion of the article (e.g. culture vessel), may be defined by a coated oxygen permeable substrate, as described herein. In some embodiments, the coated oxygen permeable substrate may form a portion of one or more sides, walls, and/or bottom of the article. In certain embodiments, the percentage of one or more sides, walls, and/or bottom of the article (e.g. culture vessel) or the entire article that is defined by the coated oxygen permeable substrate may be greater than or equal to about 1%, greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, greater than or equal to about 90%, greater than or equal to about 95%, or greater than or equal to about 97%. In some embodiments, the percentage of one or more sides, walls, and/or bottom of the article (e.g. culture vessel) or the entire article that is defined by the coated oxygen permeable substrate may be less than or equal to about 100%, less than or equal to about 95%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., greater than or equal to about 5% and less than or equal to about 90%). Other values are also possible.

As used herein the term "cell" refers to a biological cell.

As used herein the term "stem cells" has its ordinary meaning in the art and refers to embryonic stems cells as well as induced pluripotent stem cells. As used herein, embryonic stem cells are pluripotent cells isolated from the inner cell mass of blastocysts and propagated in vitro. These cells have the capacity to differentiate into any cell type in the body. Embryonic stem cells described herein therefore have been isolated from their natural environment (i.e., the blastocyst). That is, they have been physically separated from the blastocyst. In some embodiments, the embryonic stem cells are untransfected (i.e., they have not been genetically manipulated after their establishment to comprise or express an exogenous nucleic acid). In some embodiments, the embryonic stem cells do not express an antibiotic resistance gene such as the neomycin gene. In some embodiments, however, the embryonic stem cells may be genetically engineered to express one or more specific lineage differentiation factors. In certain embodiments, the embryonic stem cells are human embryonic stem cells.

As used herein, "low oxygen partial pressure" refers to partial pressures of oxygen that are less than atmospheric partial pressure.

The term "functional group," as used herein, refers to a group or moiety which is capable of being chemically modified via chemical reaction with a molecule to form a covalent bond between the functional group and a moiety or group on the molecule. Functional groups will be selected readily, by those of ordinary skill in the art, based upon the description provided herein and knowledge in the art. Those of ordinary skill in the art will be aware of suitable chemical reactions between a functional group on a surface and biological molecules. Non-limiting examples of chemical reactions include addition reactions, oxidation reactions, reduction reactions, elimination reactions, and substitution reactions. It should be understood that covalent bonds may be formed by other types of reactions, as known to those of ordinary skill in the art, using functionalizable groups.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

A protein comprises a polymer of amino acid residues linked together by peptide (amide) bonds. The term, as used herein, refers to proteins, polypeptides, and peptides of any size, structure, or function. Typically, a protein will be at least three amino acids long, preferably at least 10 amino acids in length, more preferably at least 25 amino acids in length, and most preferably at least 50 amino acids in length. Proteins may also be greater than 100 amino acids in length. A protein may refer to an individual protein or a collection of proteins. A protein may refer to a full-length protein or a fragment of a protein. Inventive proteins preferably contain only natural amino acids, although non-natural amino acids and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a myristoyl group, a fatty acid group, a linker for conjugation, functionalization, or other modification, etc. A protein may also be a single molecule or may be a multi-molecular complex comprising proteins, lipids, RNA, DNA, carbohydrates, etc. A protein may be a natural or unnatural fragment of a naturally occurring protein or peptide. A protein may be naturally occurring, recombinant, or synthetic, or any combination of these.

As used herein, the term "xenogeneic" has its ordinary meaning in the art and may refer to a composition of matter that is belonging to and/or derived from a different species. In some embodiments, the species of refer may be a human being, such that xenogeneic refers to compositions of matters belonging to and/or derived from non-humans. It should be understood that the species of refer may be non-human species, in some embodiments.

U.S. Provisional Patent Application Ser. No. 61/835,326, filed Jun. 14, 2013, and entitled "Template for Stem Cell Growth and Related Methods," is incorporated herein by reference in its entirety for all purposes.

The following examples are intended to illustrate certain embodiments of the present invention, but do not exemplify the full scope of the invention.

EXAMPLE 1

Introduction

Pluripotent stem cells hold enormous promise in drug screening applications, in vitro modeling of genetic disorders, and therapeutic replacement of diseased cells in major diseases such as heart disease, diabetes, and neural diseases such as Parkinson's, which annually affect millions of people in the United States. Thus, reproducible and scalable in vitro culture methods for human embryonic stem cells (hES) and human induced pluripotent stem cells (hiPS) could have profound implications for many fields of human health. Typical stem cell therapies and diagnostic screenings are estimated to require ~$10^9$ cells per patient. Thus, to be clinical relevant, culture methods must yield large numbers of cells, requiring demonstration on large culture format rather than micro-well platforms. The composition of the culture surface must be uniform in composition over the area of the large well plate, stable over period required for cell culture, and reproducibly fabricated.

Cell-protein interactions are essential for achieving the surface attachment of hES. Current culture method for achieving the surface attachment of hES is to coat the plate for one hour with absorbed Matrigel. This can also be completed with proteins such as fibronectin or vitronectin. After one hour the cells are then disbursed on the plate and allowed to attach over a 24 hour period of time. Cells are cultured for 5 to 7 days before they need to be removed from the surface and redistributed on a new surface. Absorbed protein surfaces can be stored at 4° C. for two weeks and cells can still attach to the surface. After this short period of time, the cells plating efficiency decreases. While the use of covalently bonding proteins to the surface increases the number of steps, plates can be stored for up 4 to 5 weeks at 4° C. and still maintain high plating efficiency. This allows for a large bank of plates to be made ahead of time for a given month and reduces the work load at each passage.

Additionally, undesirable xenogeneic proteins are introduced by common methods of culture which employ either embryonic fibroblast feeder layers or Matrigel. The Matrigel is a gelatinous protein mixture secreted by mouse tumor cells and its composition can vary from lot to lot. Culture methods employing only human proteins are desired for mimicking normal development pathways. However, approaches for producing xenogeneic free culture surfaces are in their infancy.

There is some evidence that oxygen concentration, together with cell-protein interactions, may be important for controlling differentiation and proliferation. To maintain the same oxygen level in the cell ($pO_2$ cell) as the gas phase ($pO_2$ gas) requires culturing cells on an oxygen permeability media, such as silicone rubber (SiR). However, embryonic stem cells do not attach and grow on uncoated SiR surfaces. Any surface modification of the SiR must be thin so as provide negligible resistance to oxygen permeation.

A matrix of well-defined chemical composition and long-term stability that supports the clonal growth of single hES cells on macro-scale is described. This novel matrix consists of a cross-linked hydrogel with carboxylic functional groups (—COOH) conjugated to fibronectin. The uniform —COOH functionalized layer required for covalently attaching the protein is by initiated Chemical Vapor Deposition (iCVD). iCVD coatings have not been previously used for embryonic stem cell growth. Some advantages of the iCVD approach include its stability and reproducibly over a large-scale (>1 m width) through systematic control over the deposition conditions. The iCVD method allows easy copolymerization of vinyl monomers bearing useful functional groups like carboxylic groups that can be easily covalently functionalized with peptides and proteins. The iCVD-prepared hydrogels can have a tunable cross-linking density that makes them stable under sterilization conditions and repeated use.

Additionally, iCVD allows easy tuning of the functional group density on the surface which directly relates to the density of peptides or proteins covalently bonded on the surface. When the protein layer is only adsorbed, the surface properties of the material on which the proteins are adsorbed can negatively affect both the amount and the conformation of the proteins, and in some instances adversely alter cell behavior. This approach instead, being based on strong covalent bonding of protein to the polymer coating resulted in a large window of conditions and protein surface density in which the cell growth and differentiation was efficiently promoted.

In this example, serum-free SiR surfaces were investigated in various forms: (1) unmodified, (2) chemically modified and functionalized with synthetic iCVD hydrogels, and (3) chemically modified with synthetic iCVD hydrogels to which defined proteins are attached by covalent linkage. The serum-free approach allowed any enhancement in the cell growth that was directly attributable to the solid surface. The iCVD matrix layer was grown directly on SiR membranes without dewetting or delaminating. The iCVD polymeric layers with systematically varied chemical compositions, functional group density, and density of covalently bonded proteins, were screened for their ability to promote hES proliferation while supporting pluripotency.

Results and Discussion

Figure 2:
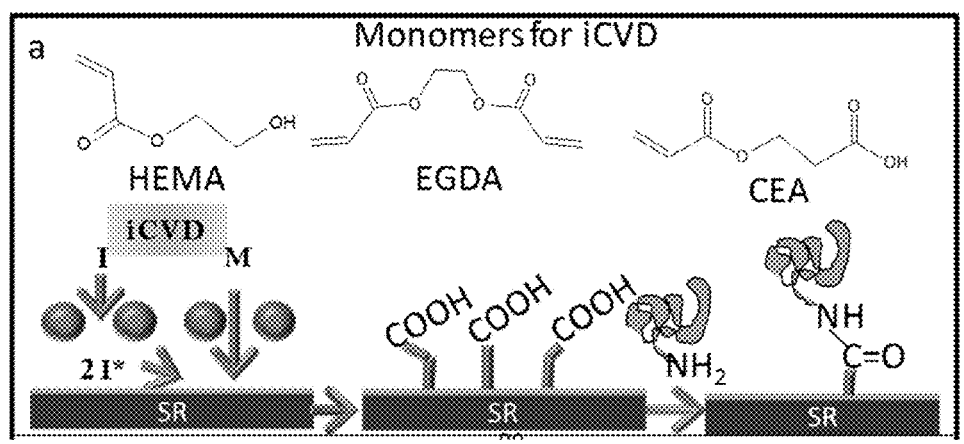
FIG. 2 shows a schematic illustration of the deposition of a matrix via initiated chemical vapor deposition, according to certain embodiments.
Figure 3:
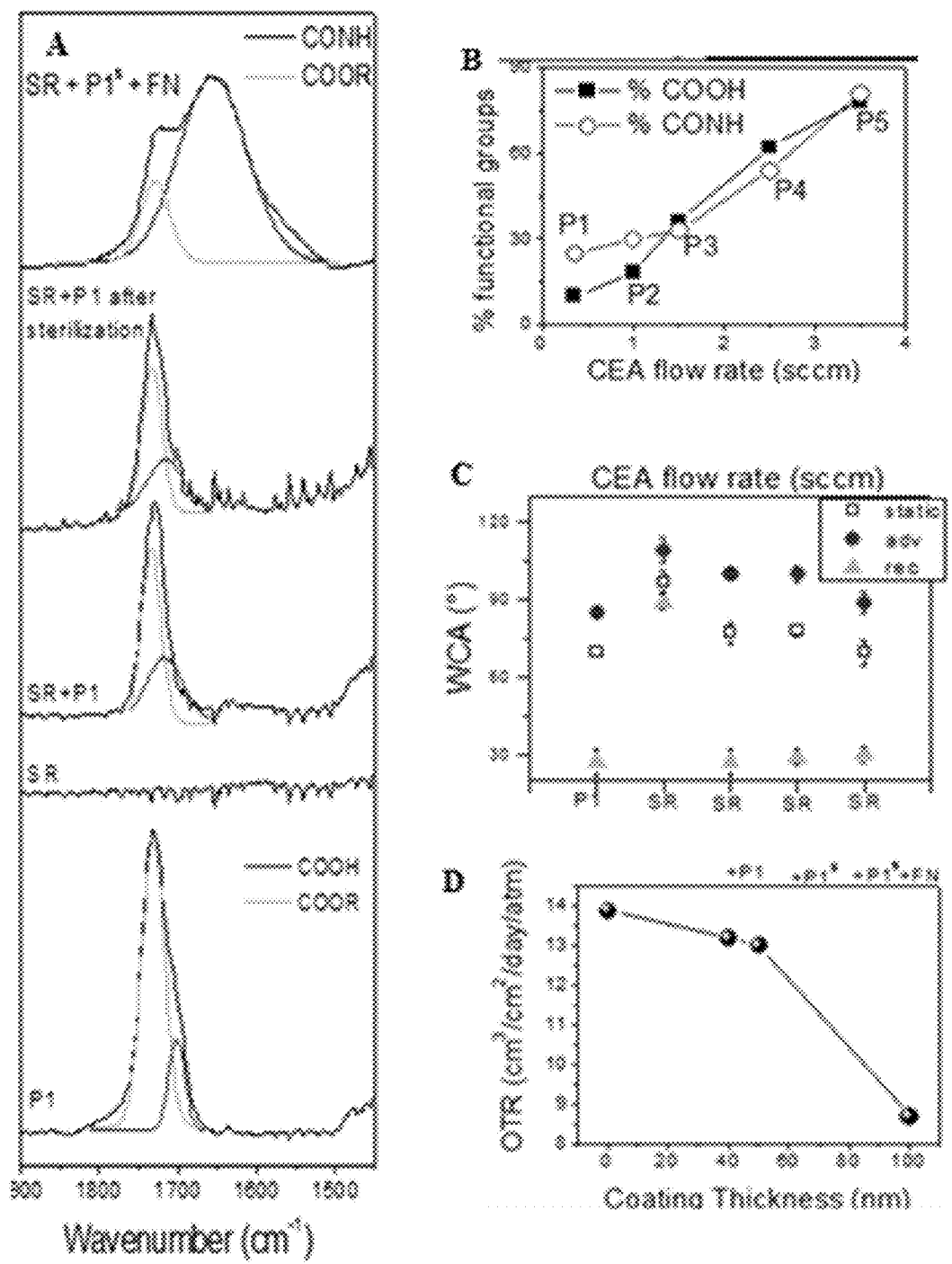
FIGS. 3A-D show (A) FTIR spectra of certain substrate surfaces, (B) a graph of the percentage of functional groups for different polymer surfaces and covalent linkages after the polymers were functionalized with proteins, (C) a graph of advancing and receding water contact angle for various substrate surfaces, and (D) a graph of oxygen transmission rates for various coating thicknesses, according to certain embodiments.

To synthesize surfaces able to covalent bind the fibronectin for promotion of cell adhesion, three acrylate monomers were copolymerized by iCVD: HEMA, EGDA and CEA (FIG. 2). FIG. 2 shows monomers used for the iCVD deposition and a schematic diagram showing the deposition of an iCVD polymer (P) containing carboxylic groups on silicon rubber (SiR) substrates and its functionalization with human fibronectin through covalent bonding. Polymers of HEMA are known for their ability to swell in water media, giving rise to hydrogels that favor cell growth. The HEMA component was also useful for achieving more moderate hydrophilicity than was possible from copolymer of CEA and EGDA alone. EGDA was added as a cross-linker to ensure stability against aging and sterilization. Finally, CEA was the monomer responsible for bearing the carboxylic acid functional groups. By changing the vapor flow rate of CEA, five polymer surfaces with different density of —COOH groups were obtain. IR analysis showed that the polymer had the characteristic signature of acrylate coatings: carbonyl absorption at 1780-1730 $cm^{-1}$, OH absorption around 3500-3000 $cm^{-1}$ and C—H absorptions (stretching at 2900-2700 $cm^{-1}$, bending around 950-850 $cm^{-1}$). The carbonyl absorption band of the P1 polymer has been enlarged in FIG. 3A and decomposed in two components assigned to the carboxylic (COOH, 1780-1710 $cm^{-1}$) and the ester (COOR, 1750-1735 $cm^{-1}$) functionalities. FIG. 3A shows the carbonyl band after every step of modification of the silicon rubber substrate. Specifically, FIG. 3A shows FT-IR absorption C═O band (1800-1600 $cm^{-1}$) of P1 polymer coating deposited on Silicon substrate and of the uncoated SiR substrate, SiR substrate coated with P1 polymer before and after sterilization, and with sterilized P1 (P1s) functionalized with fibronectin (FN). C═O band changed shape and position with the functionalization reaction due to the formation of amidic CONH bonds. The intensity of the C═O band remained unchanged after sterilization suggesting that the synthetic surfaces produced were stable to the sterilization procedure. The carbonyl absorption was detectable only after the deposition of the polymer on the SiR substrate, while it was absent in the spectrum of the bare SiR. The band had the same intensity and shape after sterilization, confirming that the functional groups and the thickness of the polymer layer survived the sterilization step.

After deposition, the —COOH groups were functionalized by reaction with —$NH_2$ groups of proteins in order to covalently bond the proteins to the surface. The formation of amidic (—CONH) groups was demonstrated by FT-IR analysis in fact a new component at 1650 $cm^{-1}$ was detected as shown in FIG. 3A. The presence of the nitrogen coming from the functionalization of the coating with the fibronectin was also detectable by XPS analysis. The quantification of the area of the COOH and CONH components (FIG. 3B) revealed that the surface containing the lowest percentage of COOH groups was the surface that bound the least amount of proteins, while the surface that had the highest surface density of COOH groups was the one that bound the most protein molecules. FIG. 3B shows a plot of the percentage of COOH groups for the different polymer surfaces and of CONH groups after the polymers were functionalized with proteins. XPS analysis showed that the protein layer was stable to aging for 5 weeks while the percentage of nitrogen dropped to zero already after two weeks when the layer of protein was adsorbed directly on the SiR and not covalently bonded.

TABLE 1

X-ray photoelectron spectroscopic elemental ratios.

| Substrate | Sample | % C | % O | % N | % Si |
|---|---|---|---|---|---|
| Si | P1 | 63 | 34 | 0 | 0 |
|  | P1 + FN | 53 | 21 | 15 | 0 |
| SR | P1 | 54 | 25 |  | 18 |
|  | P1 + FN week1 | 56 | 26 | 2 | 16 |
|  | P1 + FN week 5 | 56 | 29 | 2 | 13 |
|  | Adsorbed FN week 1 | 59 | 23 | 1 | 16 |
|  | Adsorbed FN week 2 | 62 | 22 | 0 | 16 |

Table 1 shows the X-ray photoelectron spectroscopic elemental ratio of P1 coating deposited on silicon wafer before and after functionalization with FN and elemental surface composition when the same polymer was deposited on SiR. The high mobility of SiR is the responsible of the different elemental ratios detected. The elemental composition remained unchanged after 5 weeks when the FN was covalently bonded on the surface, while when the FN was just adsorbed already after 2 weeks the percentage on N was null on the surface.

The % of silicon detected by XPS was due to the migration effects: in order to reduce the interfacial free energy the polymer does not stay on the surface but penetrates the network of the SiR. This can result in significant differences in surface chemistry when the surface is in aqueous or in dry environment. This hypothesis was confirmed by the WCA measurements reported in FIG. 3C, which shows a graph of the advancing and receding contact angles of P1, uncoated SiR, SiR coated with P1 polymer and with P1 functionalized with FN. The big differences among advancing and receding angles are due to SiR surface mobility. SiR was hydrophobic, indeed the advancing and receding CA of untreated SiR are large (109° and 89°, respectively), after the coating deposition the advancing angle remained high (~100°) and it only slightly decreased after the fibronectin bonding (89°). On the contrary, the receding contact angle decreased significantly after the polymer deposition, reaching the same value (~30°) measured for the P1 polymer deposited on Si wafer where there are no migration effects. As will be shown later the migration of the polymer inside the SiR network did not influence the cell attachment since in aqueous environment the polymer which is more hydrophilic comes up to the surface. Moderate wettability (WCA~70°, similarly to the P1 iCVD polymer) was demonstrated to be optimal for hES cell-colony formation. Finally FIG. 3D shows that the oxygen transmission rate (OTR) of the modified SIR membranes. The OTR slightly changes from 14 of the bare SiR to 9 $cm^3/m^2/day/atm$ when the coating deposited on the SiR is 100-nm-thick. The small variation from is sensed by the cells.

Figure 4:
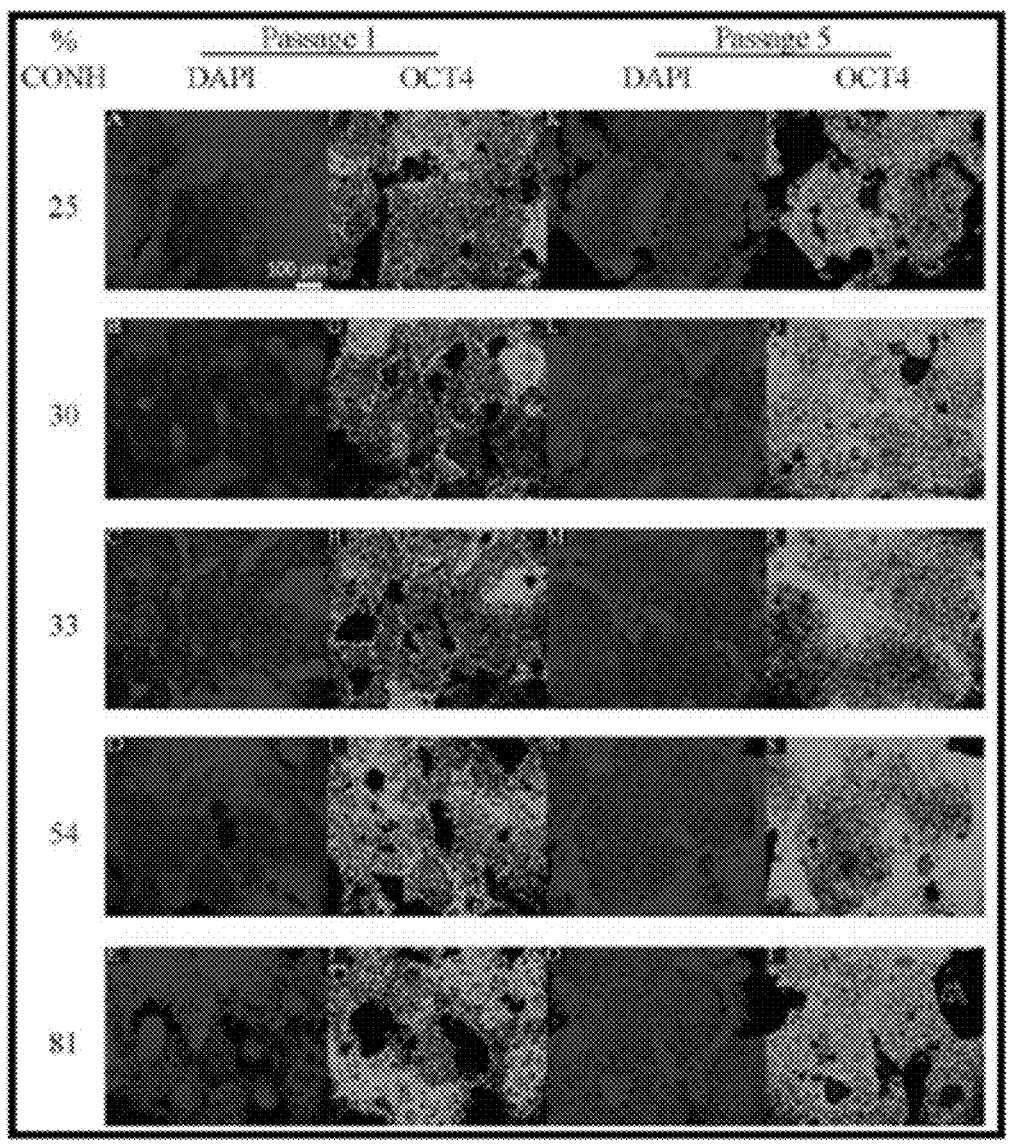
FIG. 4 shows micrographs of colonies of H7 cells cultured on the five surfaces with different percentages of covalently bonded proteins on the surface, according to certain embodiments.
Figure 5:
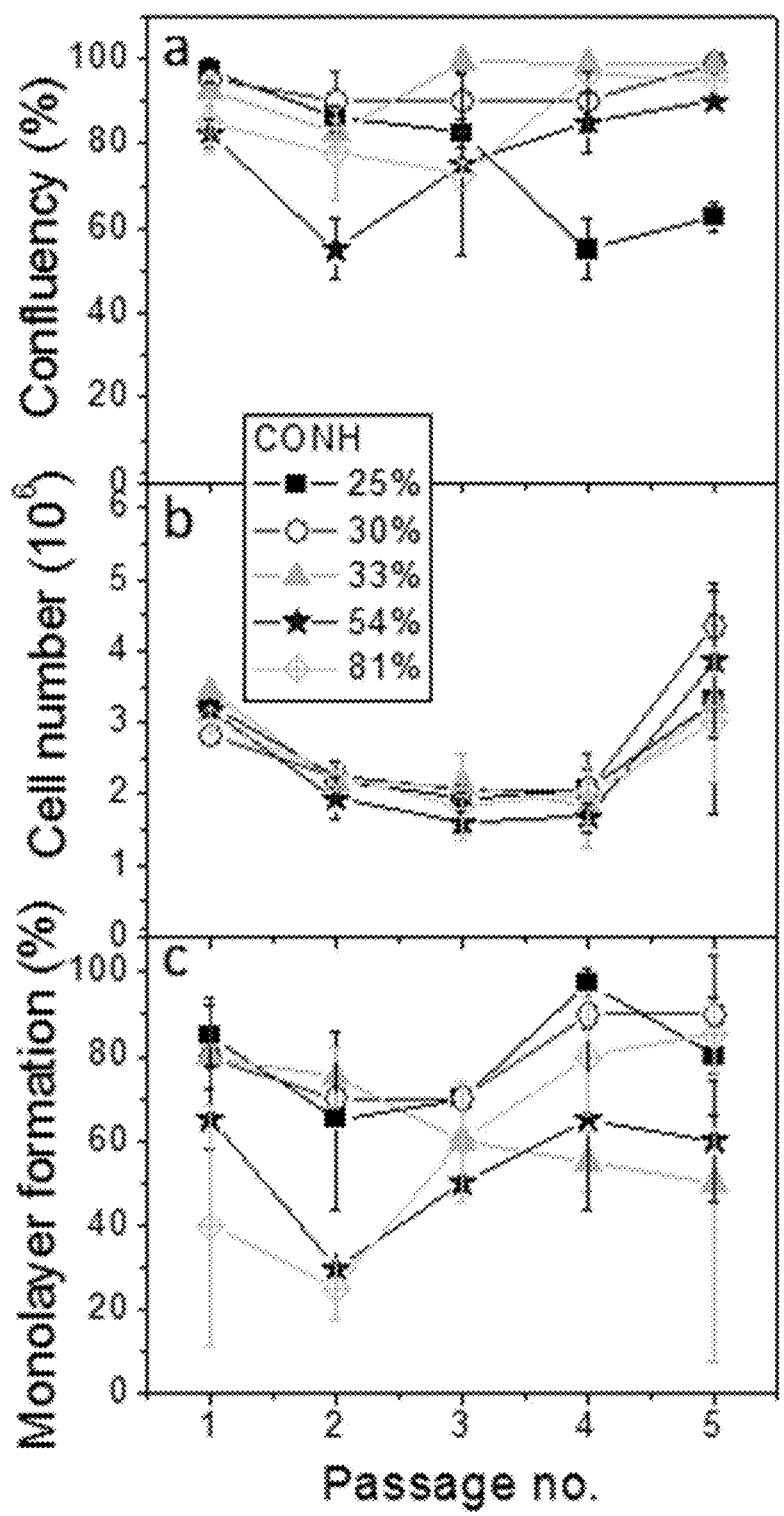
FIGS. 5A-C show graphs of the percent (A) confluency, (B) cell number, and (C) monolayer formation for various surfaces during 5 passages, according to certain embodiments.

To test the effectiveness of this approach H7 cells were cultured on the surfaces which held different percentage of CONH groups (i.e. covalent bond between the iCVD coating and the fibronectin). The percentage of CONH groups on the surface influenced the cell attachment and proliferation. As shown in FIG. 4, cell attachment was monitored with DAPI, which stains the nuclei and pluripotency was monitored with the transcription factor OCT4, which is a marker for the undifferentiated stem cells. H7 cells attached on all the surfaces and were grown for five or more passages. OCT4 expression was seen in the majority of the seeded cells over the five passages. FIG. 4 shoes micrographs of colonies of H7 cells cultured on the five polymers with increasing percentage of covalently bonded (% CONH) proteins on the surface. The cells were expressing the markers DAPI and OCT4 after one passage and five passages. At low density of bonded proteins on the surface, the cells form a nice monolayer but could not form a confluent surface. At high density of bonded proteins on the surface, the cells form agglomerates and not a monolayer. The loss of confluency and monolayer formation results in spontaneous differentiation, as evidenced by the black spots in the OCT4 images. For intermediate protein densities, the cells would form confluent monolayer on the surface, stable over more than 5 passages. The unfunctionalized hydrogel layer (i.e. without fibronectin) did not give cell attachment. FIGS. 5A-C show the plots of confluent state formation, cell number and monolayer formation for five passages along the five iCVD surface compositions explored. When the percentage of CONH was around 30% all the parameters remained stable after 5 passages. When the density of CONH groups (and consequently of proteins) on the surface was the highest (i.e.

81%), the cells formed agglomerates but did not form a uniform monolayer (FIG. 5A). All the other conditions instead resulted in high confluency which was maintained during the five passages. The cell number per well slightly increased from $1.58*10^6$ cell/$cm^2$ at passage 1 to $1.87*10^6$ cell/$cm^2$ at passage 5, averaging over the five conditions (FIG. 5B). These numbers were higher than the cell number counts on acrylate polymers synthesized by monomer printing method having only with adsorbed protein (1.3 cells/$cm^2$) and typical feeder cell layer of mouse embryonic fibroblasts ($1*10^5$ cells/$cm^2$).

When the density of the CONH groups on the surface was the lowest (i.e. 25%), the cells formed a uniform monolayer but could not form a confluent surface (FIG. 5C). The loss of confluency and monolayer formation resulted in spontaneous differentiation. For the intermediate densities of CONH groups, the cells formed a uniform confluent monolayer on the surface.

Figure 6:
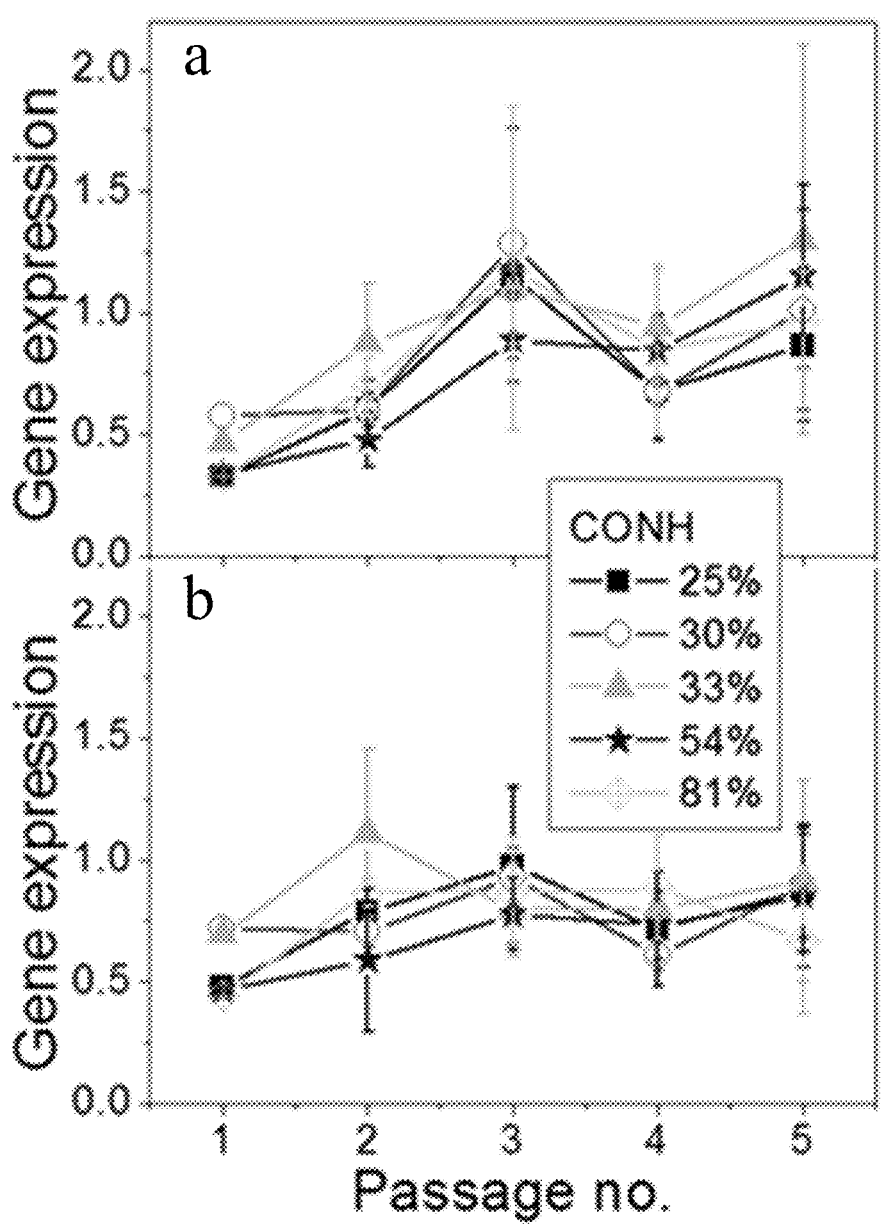
FIGS. 6A-B show graphs of gene expression of (A) OCT4 and (B) NANOG of H7 cells versus passage number for various surfaces, according to certain embodiments.

It was also demonstrated that cell morphology and phenotypic marker expression were similar for cells cultured on our iCVD coated surfaces or Matrigel. The expression levels of the hES cell markers OCT4 and NANOG were close to the unity through all the five passages and for all the percentage of CONH groups on surfaces (FIGS. 6A-B). FIGS. 6A-B shows the gene expression of OCT4 (A) and NANOG (B) relative to H7 hES cells cultured on Matrigel coated polystyrene.

Through more than 5 passages, hES cells seeded on the coated surfaces displayed an unchanged karyotype and retained pluripotency. The pluripotency was assessed by in vivo teratoma formation. Cells seeded for five passages on the iCVD coated well plates were injected intramuscularly into the flanks of SCID/beige mice. Derivatives of all the three embryonic germ layers were seen in the teratoma assays.

Karyotype analysis confirmed that the cell line had the correct number of chromosomes after >5 passages.

Conclusions

The use of iCVD to coat silicon rubber surfaces and promote serum-free embryonic stem cell adhesion was a novel approach to the goal of providing stable, xeno-free environments. iCVD coatings gave stable surfaces that survived sterilization and allowed cell proliferation for more than 5 passages. The stem cells expressed pluripotency markers and an unchanged karyotype after propagation. The synthetic iCVD surfaces that gave the best results in terms of cell attachment were the ones with intermediate density of proteins covalently bonded on the surface. The definition of this synthetic approach for stem cell culture was important for future scale-up and use of stem cell culture in actual biomedical applications. The completely synthetic nature of polymers avoided batch-to-batch variations, and the physical and chemical properties of polymers were precisely controlled and tuned.

EXAMPLE 2

This example describes the differentiation of human embryonic stem cells on coated silicon rubber substrates into beta cell precursor cells. Surprisingly, it was found that certain fibronectin densities suitable for cell attachment and maintenance inhibited directed differentiation. It was also found that certain fibronectin densities promoted directed differentiation. Stem cells differentiated on coated silicon rubber substrates having a certain density of fibronectin, had a relatively high percentage of cells at the desired beta cell precursor stage.

The differentiation was similar to the process used in Hrvatin, et al., "Differentiated human stem cells resemble fetal, not adult, β cells" PNAS 2014, except the substrate used were different. Polystyrene substrates coated with Matrigel and coated silicon rubber substrates (referred to as synthetic surface in FIG. 7) formed using the techniques described in Example 1, were used.

Figure 7:
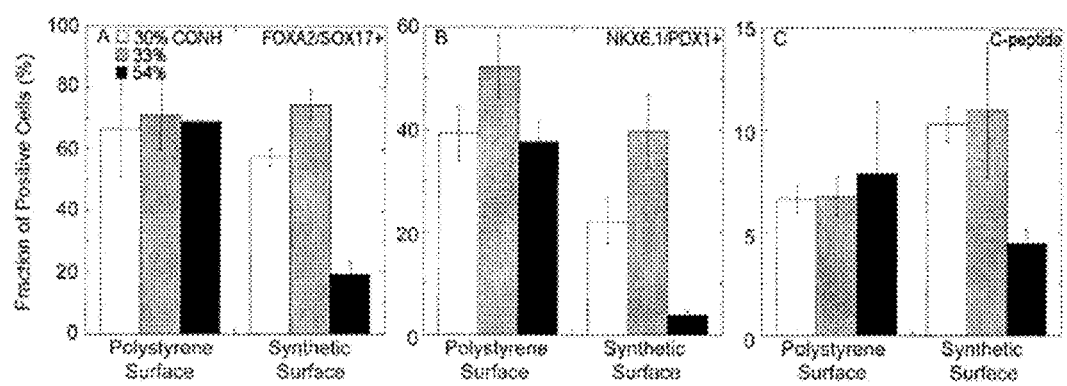
FIGS. 7A-C show graphs of the percentage cells positive for the (a) definitive endoderm makers FOXA2 & SOX17+, (B) pancreatic progenitor markers NKX6.1 & PDX1+ markers, and (C) C-peptide+ marker, according to certain embodiments.

Human embryonic stem cells were cultured on the five specific surfaces as described in Example 1. Cells cultured on three of the five surfaces were then differentiated to beta cell precursors. The three surfaces represented different surface densities of fibronectin (30, 33, and 54%). Cell were differentiated on their respective surface or on standard polystyrene culture dished coated with a layer of MatriGel. Cells proliferated on all three surfaces and then differentiated on polystyrene to beta cell precursors shown in FIG. 1. All polystyrene conditions has a greater than 50% of FOXA2 and SOX17+ cells and approximately 40% PDX1 and NKX6.1+ cells. These populations represent two of the precursors of beta cells. Only cells proliferated and differentiated on 30% or 33% were able to generate beta cell precursors. Cells proliferated and then differentiated on 54% fibronectin did not readily differentiate to beta cell precursors, as shown by the low levels of FOXA2/SOX17 staining and PDX1/NKX6.1 staining as shown in FIG. 7. FIGS. 7A-C show graphs of the percentage cells positive for the (a) definitive endoderm makers FOXA2 & SOX17+, (B) pancreatic progenitor markers NKX6.1 & PDX1+ markers, and (C) C-peptide+ marker. The markers indicated that the cells were in the immature stage as desired. The cells in the immature stage may be used to form endocrine producing cells in the pancreas. Having cells remain the NKX6.1 and PDX1 positive stage is advantage because these cells can be implanted into a body and matured in vivo.

The ability to adjust and tune the density of proteins on the surface by stable covalent bonding not only affects human embryonic stem cell proliferation but also has a profound effect on the differentiation of these cells.

EXAMPLE 3

This example describes the materials and methods used in Examples 1-2.

Polymer Synthesis.

The bottom of the wells of 24-well tissue culture treated plates was removed and replaced with silicon rubber sheets and sterilized. The interior silicon rubber surfaces were coated with five different iCVD polymer coating compositions (named as P1 to P5) that varied in the density of carboxylic groups.

The deposition chamber was described in details in previous work (see, e.g., Coclite A M, Shi Y J, and Gleason K K. Advanced Functional Materials 2012; 22(10):2167-2176). The liquid monomers (2-Carboxyethyl acrylate, CEA, Aldrich, 2-Hydroxyethyl methacrylate, HEMA, 97% Aldrich and Ethylene glycol diacrylate, EGDA, 90% Aldrich) and initiator (tert-Butyl Peroxide, TBPO, 98% Aldrich) were used without further purification. The monomers were vaporized in the liquid jars at 80° C. and were then introduced into the reactor through needle valves. The initiator was kept at room temperature and introduced through a mass flow controller (MKS Instrument). The labile peroxide bond of the initiator was thermally broken by a filament array of 14 parallel Nickel Chromium filaments (Goodfellow) at a distance of 1.5 cm from the substrate. The filament ($T_{fil}$) and the substrate temperatures ($T_{sub}$) were monitored by two thermocouples (Type K, Omega Engineering) and were 280° C. and 15° C., respectively. The substrate temperature was adjusted (with an error of ±2° C.) using a chiller/heater (NESLAB).

Table 2 lists the monomer flow rates used for the deposition of the five different (P1-P5) polymer surfaces synthesized: HEMA, EGDA and TBPO flow rates were kept constant at 0.3, 0.08 and 0.7 sccm, respectively, while CEA's flow rate varied from 0.35 to 3.5 sccm in order to vary the concentration of carboxylic groups on the surface monomer. The working pressure was maintained at 200 mTorr. Each film was deposited up to a thickness of 100±10 nm.

TABLE 2

Monomer flow rates used for the deposition of the five different (P1-P5) polymer surfaces synthesized.

| Sample | CEA (sccm) | HEMA (sccm) | EGDA (sccm) | TBPO (sccm) |
|---|---|---|---|---|
| P1 | 0.35 | 0.3 | 0.08 | 0.7 |
| P2 | 1 | | | |
| P3 | 1.5 | | | |
| P4 | 2.5 | | | |
| P5 | 3.5 | | | |

Characterization of Polymer Coatings.

Chemical characterization of the silicon rubber surface was monitored after each modification step (polymer deposition, sterilization, protein bonding) by Fourier transform infrared (FT-IR) spectroscopy through a Nexus 870 FTIR, Thermo Nicolet spectrometer equipped with a DTGS-TEC detector in attenuated total reflection (ATR) mode. The spectra were acquired from 4000 to 400 $cm^{-1}$ with a resolution of 4 $cm^{-1}$ repeating 256 scans. The reflection unit was a Germanium crystal irradiated at 65° angle. In order to minimize the effects of water vapor and carbon dioxide absorption, the spectrometer was purged with nitrogen for 15 min between each measurement. The vertical scale is always the same for all the IR spectra reported in this example. A non-linear least-squares regression was performed on the C=O stretching band (1900-1450 $cm^{-1}$) using Gaussian components using the "Fit multi-peaks" procedure of OriginLab software. The percentage of COOH or CONH functional groups was calculated from the area ratio of the fitted components. That is, the area of the desired peak (e.g., COOH, CONH) divided by the area of all groups.

Water contact angles (WCA) were measured using a goniometer equipped with an automated dispenser (Model 500, Rame-Hart). Advancing and receding angles were measured with the sessile drop method by depositing a droplet of 1 µL on the surface, then increasing the volume to 4 µL, finally decreasing it. Advancing angles were considered as the maximum angles observed during the droplet growth. Receding contact angles were measured in correspondence of the drop profile just before the contact surface reduction. Each WCA value was averaged from measurements of four drops with an estimated maximum error of 4°.

The elemental analysis was done using X-ray photoelectron spectroscopy (XPS). The XPS spectra were obtained using a SSX-100 X-probe (Surface Science Instruments) spectrometer equipped with a monochromatized Al $K_\alpha$ source, operated at 1486.8 eV. Survey scans were conducted, at take-off angles of 0° with the surface normal, to sample the surface at maximum penetration depths. During the XPS analysis, the sample charge was compensated by a 1 eV electron beam at high neutralization current by means of a Flood Gun. The pass energy was 150 V for survey scans and 50 V for high-resolution scans. The pressure during analysis was kept under $2\times10^{-9}$ Torr. A 1 mm diameter beam was used in the analysis. CasaXPS software was used to fit the high-resolution spectra. Samples were stored under vacuum overnight prior to analysis.

Permeability measurements were performed using an apparatus previously developed (see, e.g., Asatekin A and Gleason K K. Nano Letters 2011; 11 677-686).

Protein Covalent Bonding.

After depositing the coating, the plates were sterilized, in 70% ethanol for 1 h and dried overnight under a germicidal UV lamp. Human fibronectin (0.1%, Aldrich) was then covalently bonded to the carboxylic groups of the polymer coating. The well plates were incubated for 30 min at room T with N-(3-Dimethylaminopropyl)-N'-ethylcarbodiimide (EDC, 97%, Aldrich) (0.5 mg/mL) in $NaH_2PO_4$ buffer (0.03M), pH 5. After aspiration of the EDC solution, the samples were incubated again with 1 mM of fibronectin in phosphate buffer (pH7.4) for 1 h and then washed with phosphate buffer (pH 7.4).

Cell Culture.

The ability to promote attachment and proliferation of undifferentiated hESC was tested. H7 cells were seeded and enumerated. H7 hESC were maintained in the chemically defined medium mTeSIR™1 (Stemcell Technologies). Cultures were passaged every 4-6 days, as cell became ~90% confluent. Seeding density was ~150,000 cells/$cm^2$. Cells received fresh medium every day. Cultures were routinely examined by Immunocytochemisty for the expression of hESC markers. Cytogenetic analysis by G-banding for normal karyotype was performed before the beginning of the experiment and at the duration of the experiment.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article for use in stem cells differentiation, comprising:

an oxygen permeable substrate having at least a portion of a surface coated with a synthetic matrix having an average thickness of less than 90 nm, wherein the synthetic matrix is covalently crosslinked, between about 30% and about 80% of all groups on the surface of the synthetic matrix are amide bond groups, and biological molecules are covalently bound to the surface of the synthetic matrix via the amide bonds, and wherein the oxygen permeability/thickness of the article is greater than or equal to about $250 \times 10^{-14}$ mol $\sec^{-1}$ $cm^{-2}$ mm $Hg^{-1}$.

2. The article of claim 1, wherein the synthetic matrix is a hydrogel.

3. The article of claim 1, wherein the oxygen permeable substrate is free of non-human material.

4. The article of claim 1, wherein the synthetic matrix consists essentially of synthetic polymers.

5. The article of claim 1, wherein between about 30% and about 54% of a surface of the synthetic matrix is covalently bound to the biological molecules.

6. The article of claim 1, wherein the oxygen permeability/thickness of the oxygen permeable substrate coated with the synthetic matrix is at least about 80% of the oxygen permeability/thickness of an essentially identical oxygen permeable substrate lacking the matrix.

7. The article of claim 1, wherein the oxygen permeable substrate is a silicon rubber.

8. The article of claim 1, wherein the biological molecules are proteins.

9. The article of claim 1, wherein the percent of the amide bonds on the surface of the matrix is between about 30% and about 54%.

10. The article of claim 1, wherein the shelf life of the article is greater than or equal to 2.5 weeks.

11. The article of claim 1, wherein the synthetic matrix comprises acrylates.

12. The article of claim 1, wherein the synthetic matrix is a hydrogel comprising covalently crosslinked acrylate polymers.

13. The article of claim 12, wherein the synthetic matrix comprises carboxylic acid groups on the surface of the synthetic matrix.

* * * * *